US009999497B2

(12) United States Patent
Shiuey

(10) Patent No.: US 9,999,497 B2
(45) Date of Patent: Jun. 19, 2018

(54) CORNEAL IMPLANTS AND METHODS AND SYSTEMS FOR PLACEMENT

(76) Inventor: Yichieh Shiuey, San Jose, CA (US)

( * ) Notice: Subject to any disclaimer, the term of this patent is extended or adjusted under 35 U.S.C. 154(b) by 904 days.

(21) Appl. No.: 12/405,900

(22) Filed: Mar. 17, 2009

(65) Prior Publication Data

US 2010/0069915 A1 Mar. 18, 2010

Related U.S. Application Data

(63) Continuation-in-part of application No. PCT/US2008/061656, filed on Apr. 25, 2008, which is a continuation-in-part of application No. 11/741,496, filed on Apr. 27, 2007, now Pat. No. 8,029,515, which is a continuation-in-part of application No. 11/341,320, filed on Jan. 26, 2006, now abandoned.

(60) Provisional application No. 60/648,949, filed on Jan. 31, 2005.

(51) Int. Cl.
*A61F 2/14* (2006.01)
*A61F 2/16* (2006.01)

(52) U.S. Cl.
CPC .............. *A61F 2/142* (2013.01); *A61F 2/148* (2013.01); *A61F 2002/1699* (2015.04)

(58) Field of Classification Search
CPC .. A61F 2002/1697; A61F 2/142; A61F 2/143; A61F 2/146
USPC .................................. 623/5.11–5.16; 606/107
See application file for complete search history.

(56) References Cited

U.S. PATENT DOCUMENTS

| 4,586,929 | A |   | 5/1986  | Binder |
|-----------|---|---|---------|--------|
| 4,612,012 | A | * | 9/1986  | White ........................... 623/5.14 |
| 4,646,720 | A | * | 3/1987  | Peyman et al. ............... 128/897 |
| 4,706,666 | A |   | 11/1987 | Sheets |
| 4,842,599 | A | * | 6/1989  | Bronstein .................... 623/5.15 |
| 4,865,601 | A | * | 9/1989  | Caldwell et al. ............. 623/5.14 |
| 4,919,130 | A |   | 4/1990  | Stoy et al. |
| 5,112,350 | A |   | 5/1992  | Civerchia et al. |
| 5,211,660 | A |   | 5/1993  | Grasso |
| 5,258,024 | A | * | 11/1993 | Chavel et al. ............... 623/5.16 |
| 5,269,812 | A |   | 12/1993 | White |
| 5,292,514 | A | * | 3/1994  | Capecchi et al. ............. 424/422 |
| 5,300,116 | A |   | 4/1994  | Chirila |
| 5,344,449 | A |   | 9/1994  | Christ et al. |
| 5,474,562 | A |   | 12/1995 | Orchowski et al. |
| 5,489,301 | A | * | 2/1996  | Barber ........................ 623/5.11 |
| 5,507,806 | A | * | 4/1996  | Blake ........................... 623/6.33 |

(Continued)

FOREIGN PATENT DOCUMENTS

CN 1091000 A 8/1994
CN 2374154 Y 4/2000

(Continued)

OTHER PUBLICATIONS

U.S. Appl. No. 13/189,337, filed Jul. 22, 2011, Shiuey.

(Continued)

*Primary Examiner* — Gregory Anderson
*Assistant Examiner* — Sarah Simpson
(74) *Attorney, Agent, or Firm* — Goldberg Cohen LLP

(57) ABSTRACT

A system comprising a hollow member is used to deliver a constrained corneal implant into a corneal pocket. The hollow member may be tapered and the system may further include an implant deformation chamber and an axial pusher to advance the implant through the hollow member.

16 Claims, 16 Drawing Sheets

(56) References Cited

U.S. PATENT DOCUMENTS

| | | | |
|---|---|---|---|
| 5,522,888 A * | 6/1996 | Civerchia | 623/5.16 |
| 5,698,192 A | 12/1997 | Goldberg | |
| 5,702,441 A | 12/1997 | Zhou | |
| 5,755,785 A | 5/1998 | Rowsey et al. | |
| 5,868,752 A | 2/1999 | Makker et al. | |
| 5,919,197 A | 7/1999 | McDonald | |
| 6,050,999 A | 4/2000 | Paraschac et al. | |
| 6,106,552 A * | 8/2000 | Lacombe et al. | 623/5.14 |
| 6,162,229 A | 12/2000 | Feingold et al. | |
| 6,254,637 B1 | 7/2001 | Lee et al. | |
| 6,361,560 B1 * | 3/2002 | Nigam | 623/5.14 |
| 6,454,800 B2 | 9/2002 | Dalton et al. | |
| 6,543,453 B1 * | 4/2003 | Klima et al. | 128/898 |
| 6,579,918 B1 | 6/2003 | Auten et al. | |
| 6,592,621 B1 | 7/2003 | Domino | |
| 6,626,941 B2 | 9/2003 | Nigam | |
| 6,641,589 B2 | 11/2003 | Kita | |
| 6,685,740 B2 | 2/2004 | Figueroa et al. | |
| 6,689,165 B2 | 2/2004 | Jacob et al. | |
| 6,712,848 B1 | 3/2004 | Wolf et al. | |
| 6,786,926 B2 | 9/2004 | Peyman | |
| 6,814,755 B2 * | 11/2004 | LaCombe et al. | 623/5.14 |
| 6,824,266 B2 | 11/2004 | Jethmalani et al. | |
| 6,702,807 B2 | 12/2004 | Peyman et al. | |
| 6,827,440 B2 | 12/2004 | Ocampo | |
| 6,855,163 B2 | 2/2005 | Peyman | |
| 6,858,033 B2 | 2/2005 | Kobayashi | |
| 6,875,232 B2 | 4/2005 | Nigam | |
| 6,976,997 B2 | 12/2005 | Noolandi et al. | |
| 7,276,071 B2 | 10/2007 | Lin et al. | |
| 7,364,674 B1 | 4/2008 | Hoover | |
| 2001/0008977 A1 | 7/2001 | Portney | |
| 2002/0010510 A1 * | 1/2002 | Silvestrini | 623/5.12 |
| 2002/0022881 A1 | 2/2002 | Figueroa et al. | |
| 2002/0055753 A1 | 5/2002 | Silvestrini et al. | |
| 2002/0116056 A1 * | 8/2002 | Kirk | 623/5.11 |
| 2003/0025873 A1 | 2/2003 | Ocampo | |
| 2003/0050646 A1 | 3/2003 | Kikuchi et al. | |
| 2003/0054109 A1 | 3/2003 | Quinn et al. | |
| 2003/0093083 A1 | 5/2003 | Peyman | |
| 2003/0173691 A1 | 9/2003 | Jethmalani et al. | |
| 2003/0229303 A1 | 12/2003 | Haffner et al. | |
| 2004/0049268 A1 | 3/2004 | Noolandi et al. | |
| 2004/0073303 A1 * | 4/2004 | Schanzlin et al. | 623/5.16 |
| 2004/0199174 A1 | 10/2004 | Herberger et al. | |
| 2004/0243159 A1 | 12/2004 | Shiuey | |
| 2004/0243160 A1 | 12/2004 | Shiuey et al. | |
| 2004/0243231 A1 * | 12/2004 | Koziol | 623/5.12 |
| 2005/0080484 A1 * | 4/2005 | Marmo et al. | 623/5.14 |
| 2005/0080485 A1 * | 4/2005 | Nigam | 623/5.16 |
| 2005/0119737 A1 | 6/2005 | Bene et al. | |
| 2006/0064077 A1 | 3/2006 | Peyman | |
| 2006/0083773 A1 | 4/2006 | Myung et al. | |
| 2006/0134050 A1 | 6/2006 | Griffith et al. | |
| 2006/0173539 A1 | 8/2006 | Shiuey | |
| 2006/0235428 A1 | 10/2006 | Silvestrini | |
| 2006/0235430 A1 | 10/2006 | Le et al. | |
| 2006/0235513 A1 | 10/2006 | Price | |
| 2006/0252981 A1 | 11/2006 | Matsuda et al. | |
| 2007/0129797 A1 | 6/2007 | Lang et al. | |
| 2007/0244559 A1 | 10/2007 | Shiuey | |

FOREIGN PATENT DOCUMENTS

| | | |
|---|---|---|
| EP | 0333344 A2 | 9/1989 |
| EP | 0333344 A3 | 10/1989 |
| JP | H 4-158859 | 6/1992 |
| JP | 10-309294 A | 11/1998 |
| JP | 2002-533159 | 10/2002 |
| JP | 2002-537895 A | 11/2002 |
| JP | 2003-070829 | 3/2003 |
| JP | 2003-534070 A | 11/2003 |
| WO | WO 99/07309 A1 | 2/1999 |
| WO | WO 01/13972 A1 | 3/2001 |
| WO | WO 2003/105725 A2 | 12/2003 |
| WO | WO 2003/105725 A3 | 6/2004 |
| WO | WO 2004/105585 A2 | 12/2004 |
| WO | WO 2006/083708 A2 | 8/2006 |
| WO | WO 2006/113634 A2 | 10/2006 |
| WO | WO 2008/134573 | 11/2008 |
| WO | WO 2006/083708 A3 | 4/2009 |

OTHER PUBLICATIONS

European search report and opinion dated Dec. 5, 2011 for 08780570.1.
European search report and opinion dated Dec. 8, 2011 for 11181836.5.
European search report and opinion dated Mar. 20, 2012 for Ep Application No. 06719673.3.
International search report and written opinion dated May 1, 2008 for PCT/US2006/002918.
International search report and written opinion dated Sep. 16, 2008 for PCT/US2008/061656.
Office action dated Nov. 19, 2009 for U.S. Appl. No. 11/341,320.
Office action dated Apr. 6, 2010 for U.S. Appl. No. 11/741,496.
Office action dated May 12, 2009 for U.S. Appl. No. 11/341,320.
Office action dated Jul. 9, 2009 for U.S. Appl. No. 11/741,496.
Office action dated Aug. 13, 2012 for U.S. Appl. No. 13/189,337.
Office action dated Aug. 19, 2010 for U.S. Appl. No. 11/741,496.
Office action dated Dec. 28, 2010 for U.S. Appl. No. 11/741,496.
Crawford, Geoffrey J. et al., Two cases of AlphaCor Surgery Performed Using a Small Incision Technique, Clinical and Experimental Ophthalmology, Feb. 2005, vol. 33(1), pp. 10-15.
Sivertsen, Katrine, Polymer Foams, 3.064 Polymer Physics, Spring 2007, Massachusetts Institute of Technology.

* cited by examiner

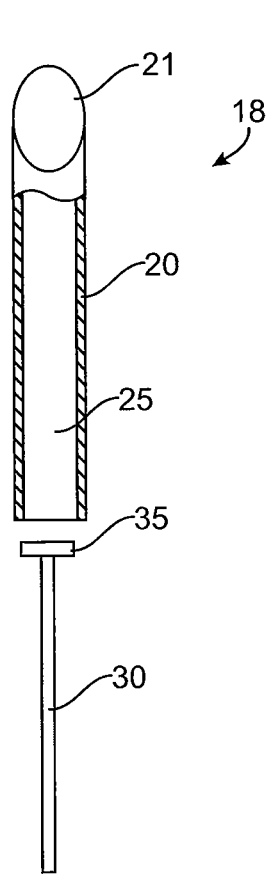
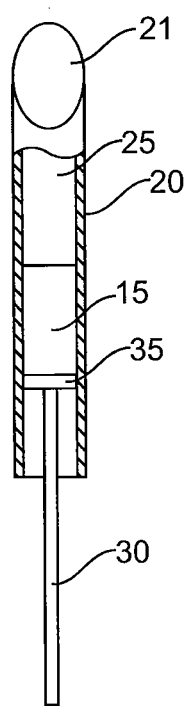
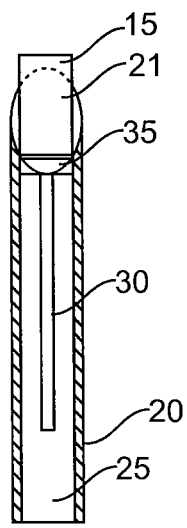
FIG. 2A   FIG. 2B   FIG. 2C
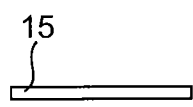
FIG. 3A   FIG. 3B   FIG. 3C

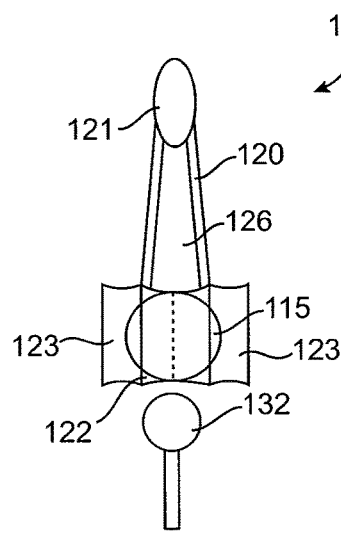
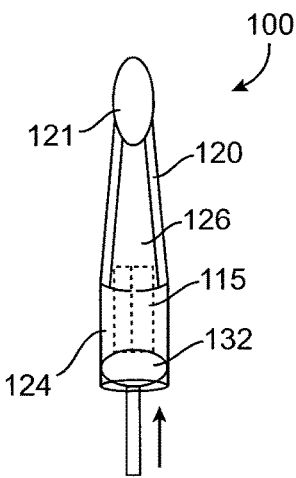
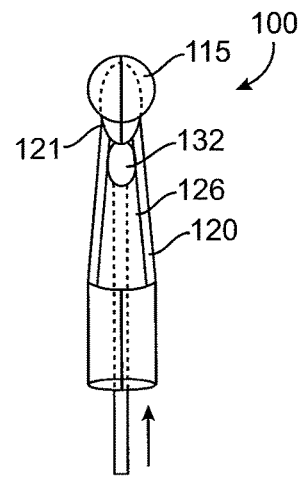
FIG. 6A        FIG. 6B        FIG. 6C
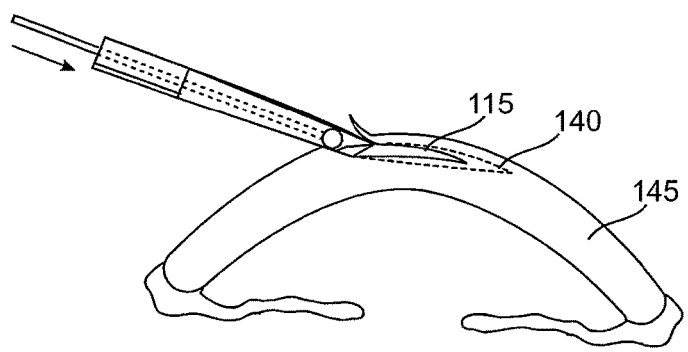
FIG. 7A
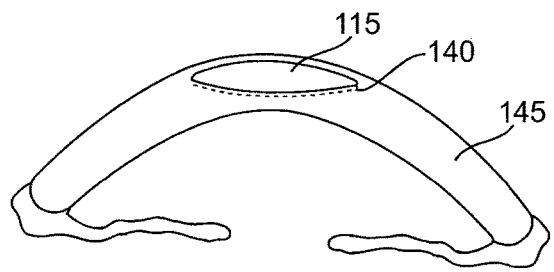
FIG. 7B

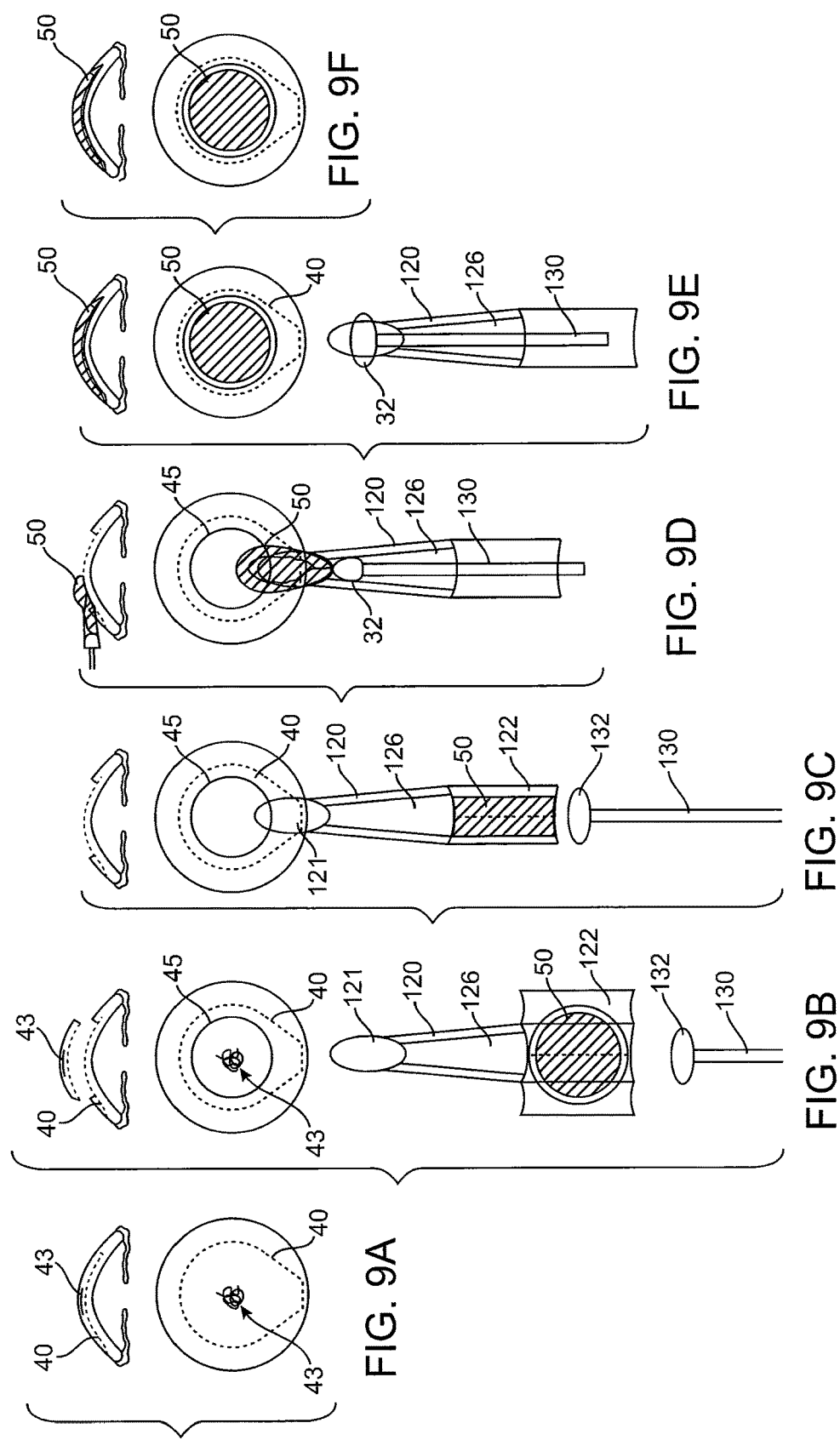

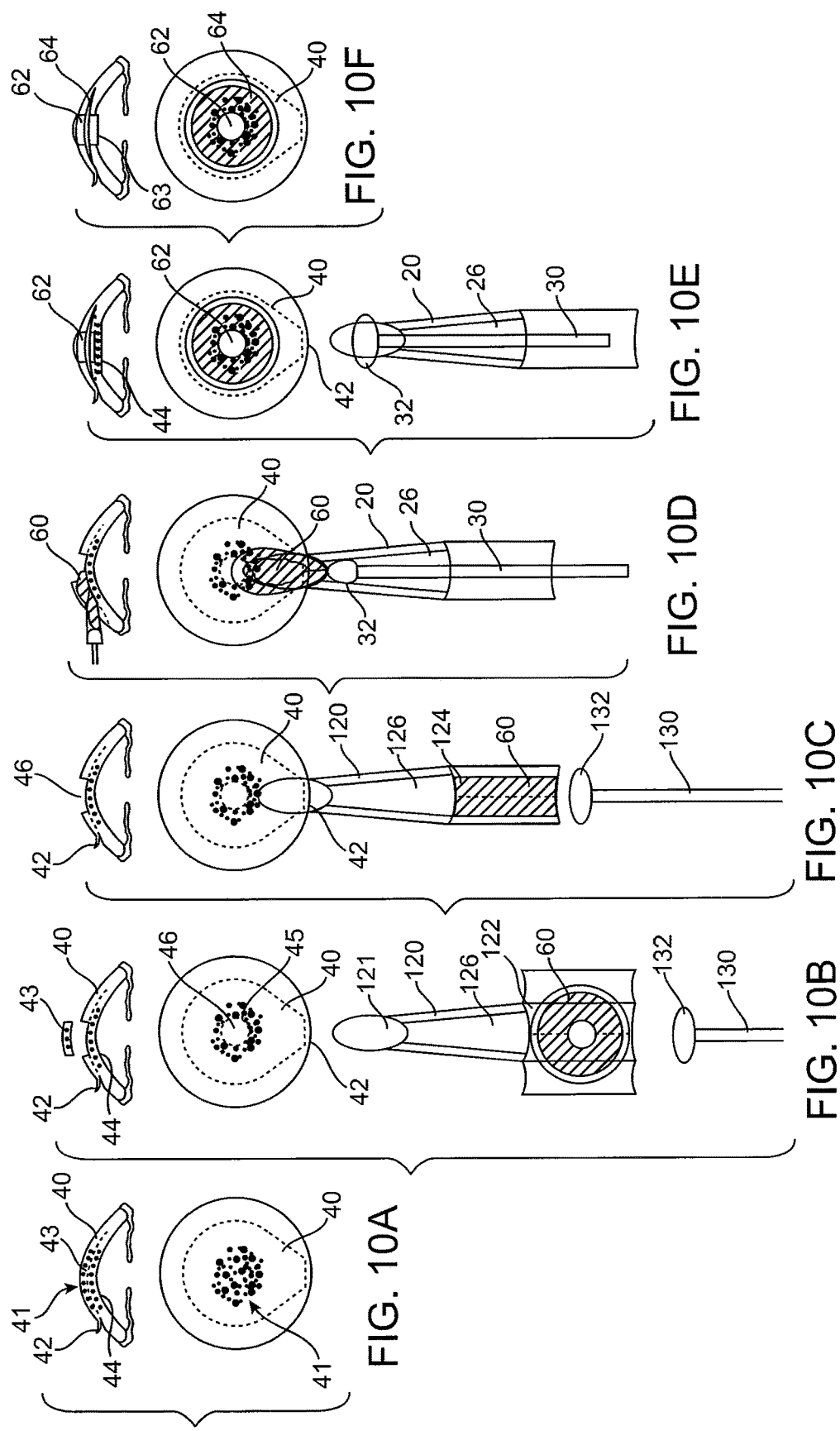

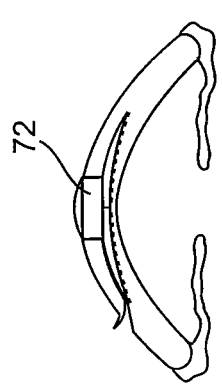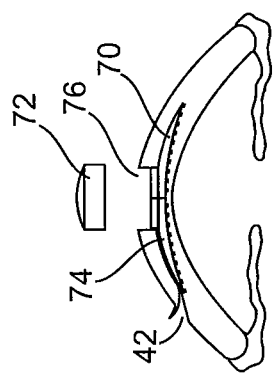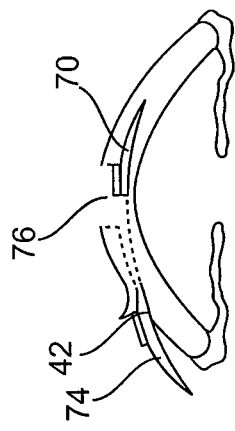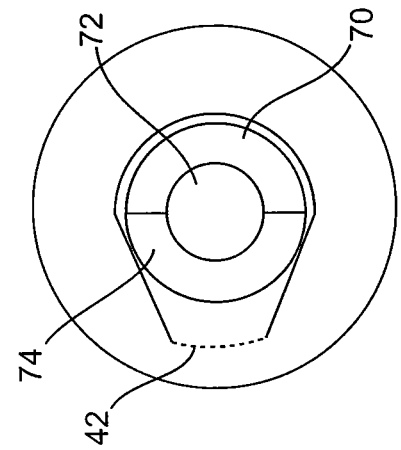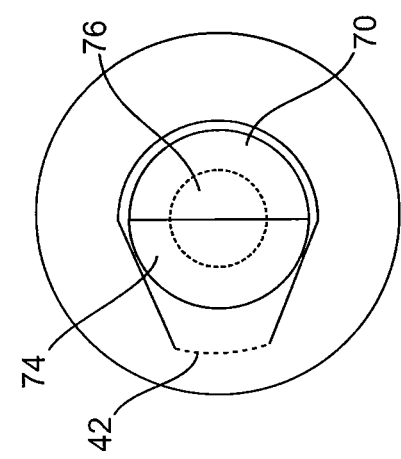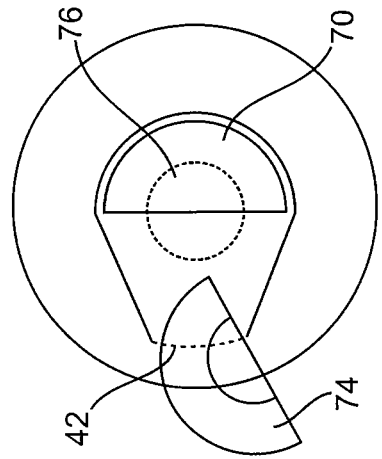
FIG. 11A  FIG. 11C  FIG. 11E
FIG. 11B  FIG. 11D  FIG. 11F

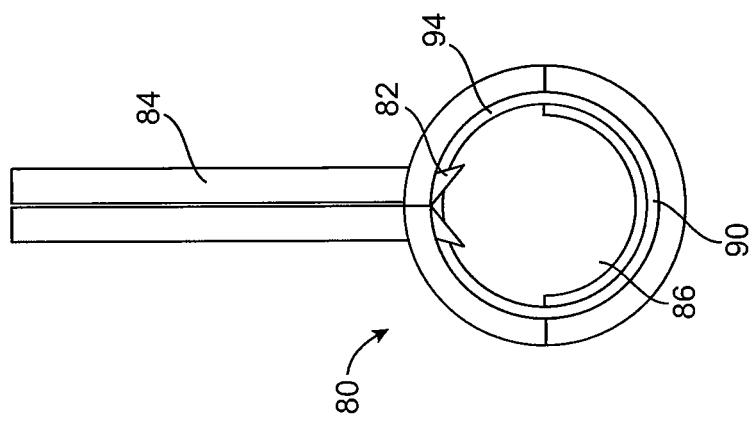
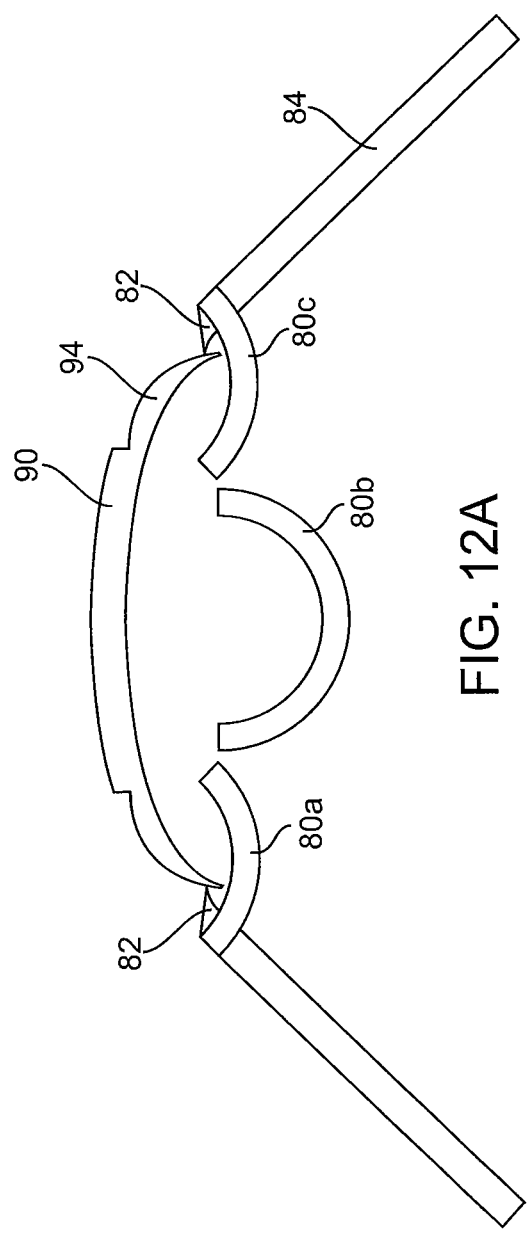
FIG. 12B
FIG. 12A

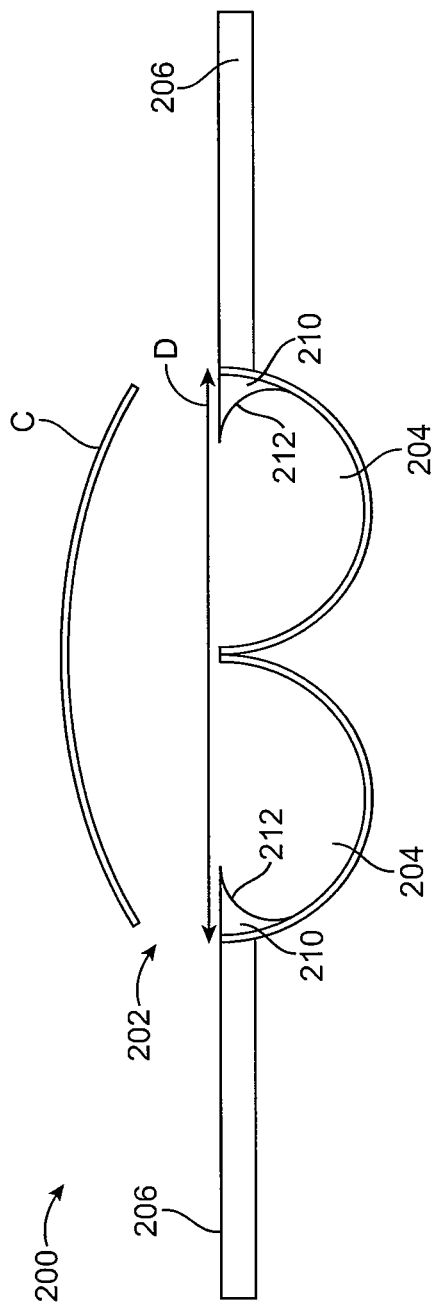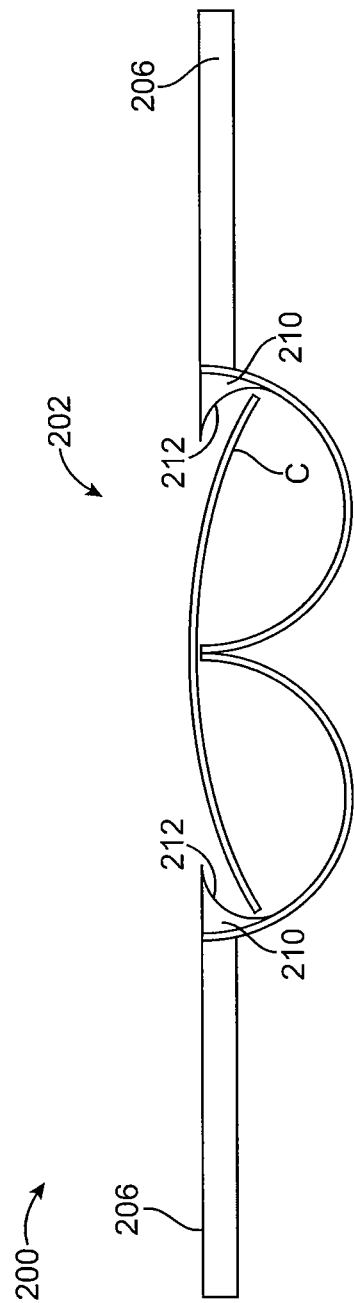
FIG. 13A
FIG. 13B

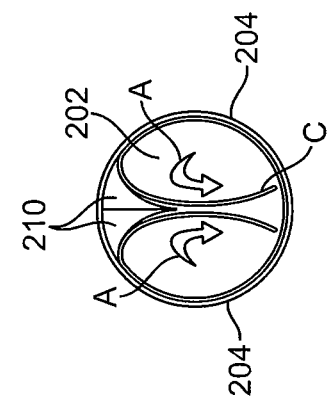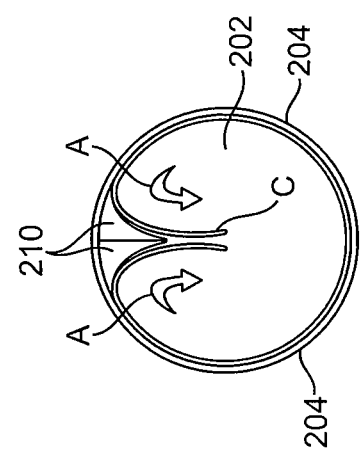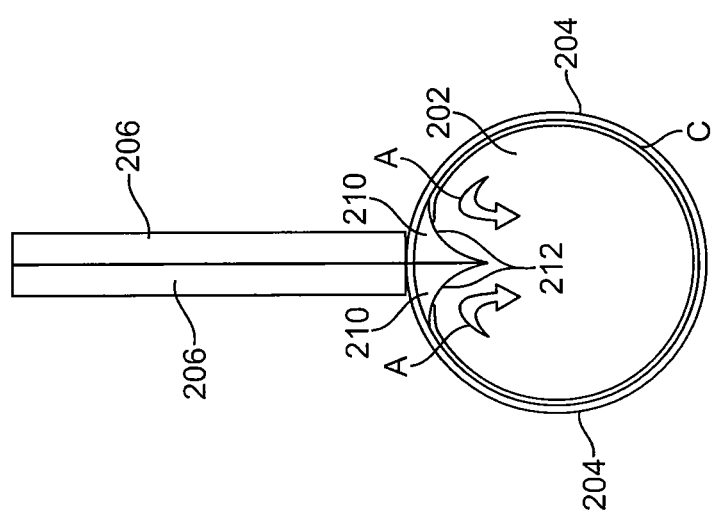

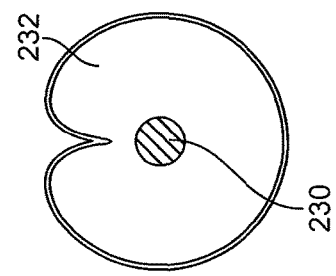
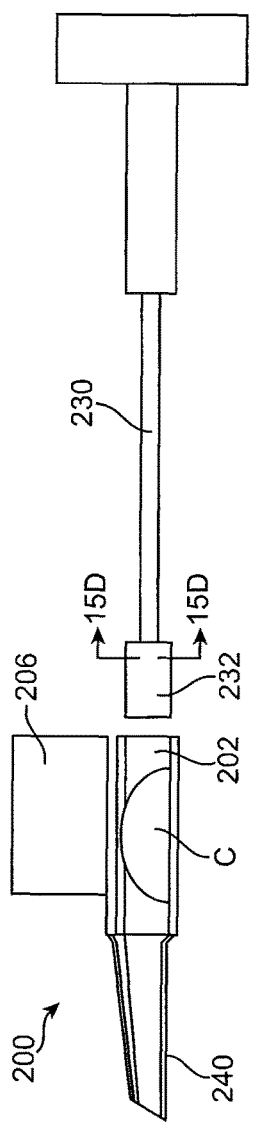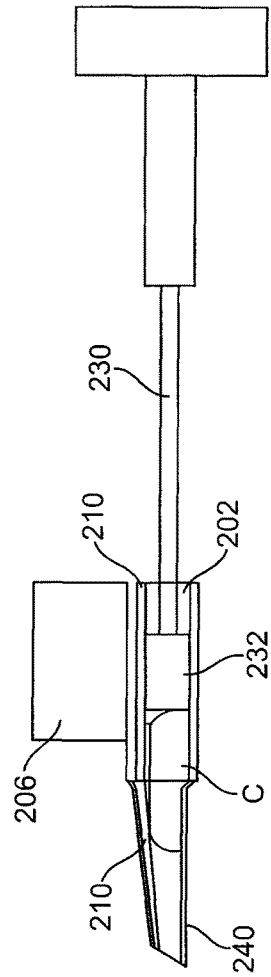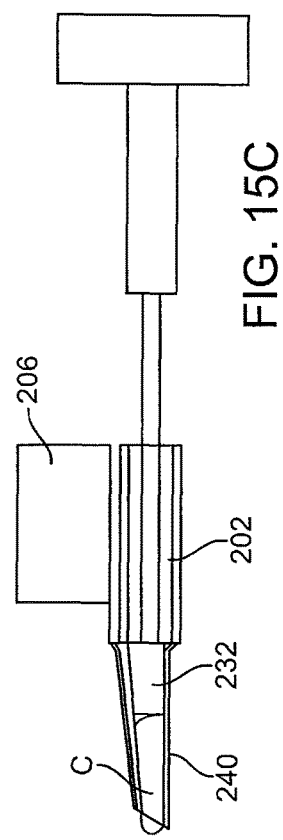

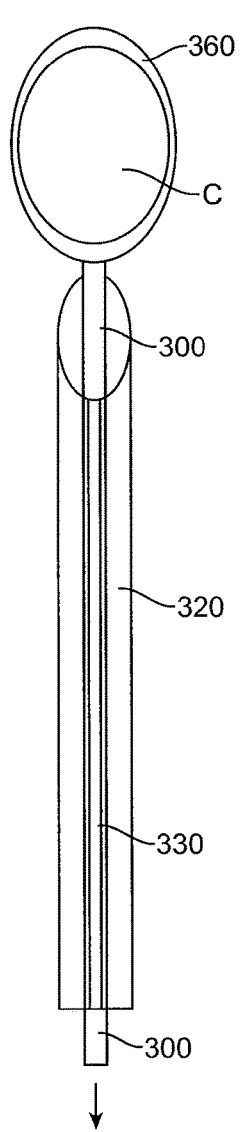 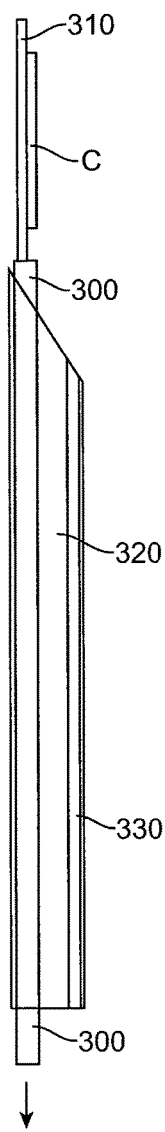 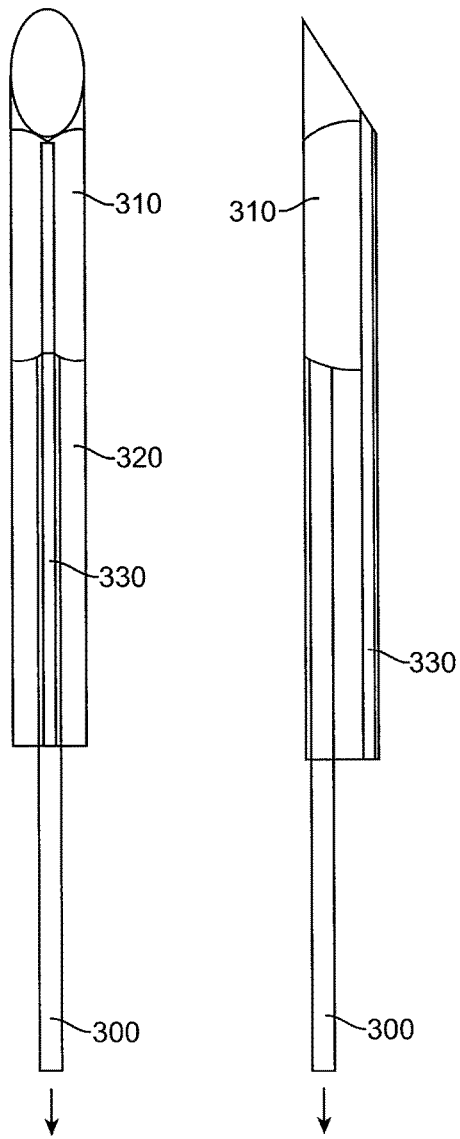 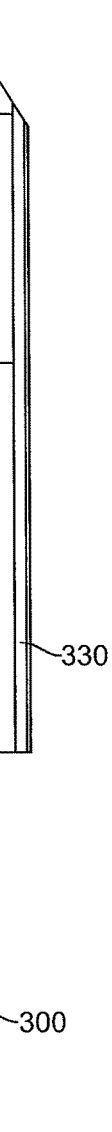
FIG. 16A  FIG. 16B  FIG. 16C  FIG. 16D
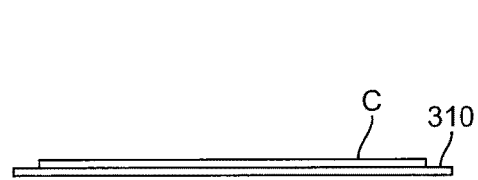
FIG. 16E
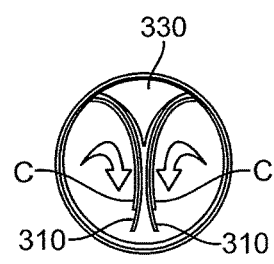
FIG. 16F

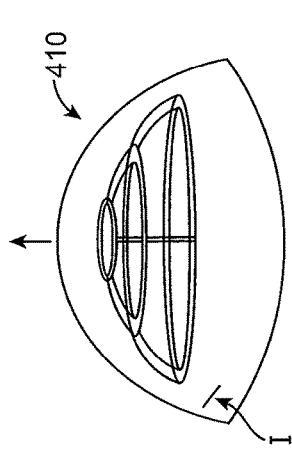
FIG. 18B
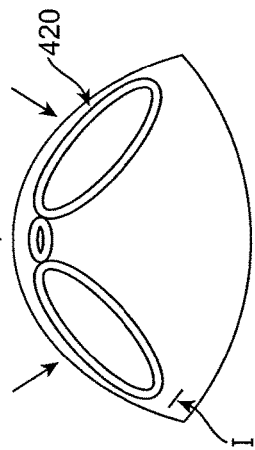
FIG. 19B
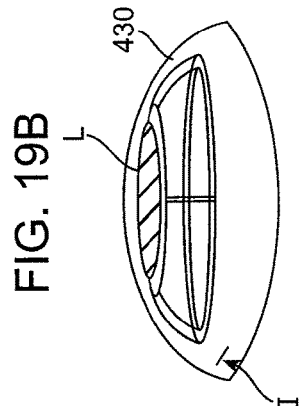
FIG. 20B
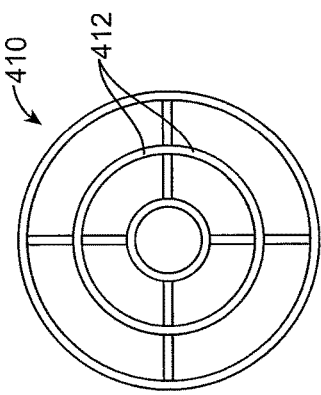
FIG. 18A
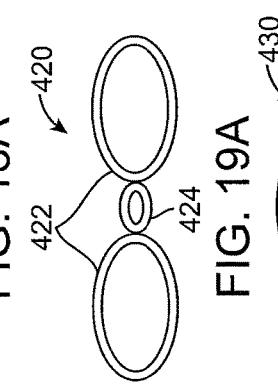
FIG. 19A
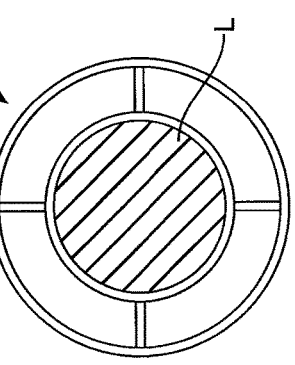
FIG. 20A
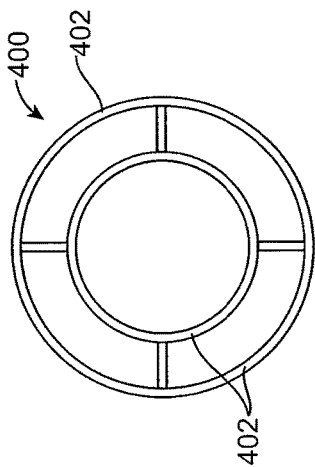
FIG. 17A
FIG. 17B
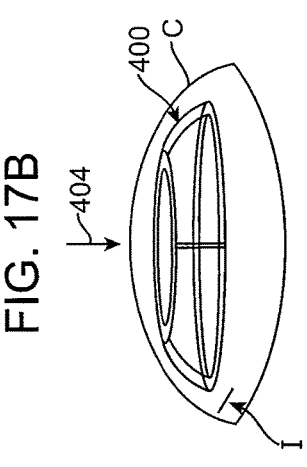
FIG. 17C

CORNEAL IMPLANTS AND METHODS AND SYSTEMS FOR PLACEMENT

CROSS REFERENCES TO RELATED APPLICATIONS

This application is a continuation-in-part of PCT/US08/61656, filed on Apr. 25, 2008, which was a continuation-in-part of application Ser. No. 11/741,496, filed on Apr. 27, 2007, now U.S. Pat. No. 8,029,515 which was a continuation-in-part of application Ser. No. 11/341,320, filed on Jan. 26, 2006, now abandoned which claimed the benefit of provisional application No. 60/648,949, filed on Jan. 31, 2005, the full disclosures of which are incorporated herein by reference.

BACKGROUND OF THE INVENTION

1. Field of the Invention

There are many different types of corneal implants that have been developed for the treatment of refractive error and disease. Because of limitations in the methods of creating corneal pockets, these implants have all been designed for placement in the cornea by creation of a corneal incision which is either similar in size to the smallest dimension of the implant or larger. Recently, two methods of corneal pocket creation have been devised which can create a pocket with an external opening width that is less than the maximum internal width of the pocket. These two methods are pocket creation by the femtosecond laser and, of particular interest, cornea cutting, as described in US 2004/0243159 and 0243160, invented by the inventor herein, the full disclosure of which is incorporated herein by reference.

It is advantageous to have a biocompatible corneal implant that can be placed through an external incision that is less than the width of the implant, especially an external incision that is less than half of the width of the implant. It is particularly advantageous if the corneal implant can be placed through an incision that does not require suturing for closure, typically being 3 mm or less. Such a small external incision also decreases induced surgical astigmatism and speeds up the recovery time for the patient. Moreover, it is useful to have a relatively large implant that can be placed through a relatively small incision. For example a lens implant that is larger is more likely to give good quality vision especially in a patient with large pupils. It is also advantageous to have a simple and reliable delivery system for the corneal implant.

Intraocular lenses (IOL's) for cataract surgery have been designed to be placed through a small incision. These small incision cataract surgery lenses cannot practically be used within a corneal pocket. Most small incision cataract surgery lens implants are usually too thick to be placed within a corneal pocket. For example the typical thickness of a cataract surgery lens implant is 1 mm or more which is substantially thicker than the human cornea, which is usually between 0.5 to 0.6 mm. Some corneal implants that have been designed only have a thickness of about 0.05 mm. Moreover, the cataract surgery lens implants have haptics, which are extensions from the lens implant designed to keep the lens implant fixated within the capsular bag. Haptics are not present and not necessary for corneal implants. Finally, the cataract surgery lens implants are not designed to be biocompatible with the cornea and would not be tolerated as corneal implants.

The delivery systems designed for small incision cataract surgery lens implants are not well adapted for use as a delivery system for small incision corneal implants. These delivery systems have been designed for cataract surgery lens implants that are much thicker than the usual corneal implant. The delivery systems for small incision cataract surgery lens implants are designed to accommodate haptics, which would not be present on a corneal lens implant. It has been found that at least some commercially available corneal implants are destroyed when placed through a standard IOL injector. Similarly, biological corneal implants placed through a standard IOL injector will often show severe histological damage, such as endothelial damage.

Corneal implants can be made of either synthetic materials (e.g. prostheses) or can be biological in origin (e.g. transplant grafts). Recently two new surgical techniques for placement of a lamellar corneal stromal endothelial transplant grafts have been devised. These surgical techniques are useful in the treatment of endothelial diseases of the cornea such as Fuchs' endothelial dystrophy and pseudophakic bullous keratopathy. One of these techniques is referred to as deep lamellar endothelial keratoplasty (DLEK). In this technique a pocket is made within the cornea and diseased corneal endothelium is excised along with a layer of corneal stroma. Healthy lamellar corneal stromal endothelial tissue is then transplanted into the space left by the excised diseased tissue. Another technique is called Descemet's stripping automated endothelial keratoplasty (DSAEK or DSEK). In this technique, a lamellar corneal stromal endothelial transplant graft is automatically created using either a microkeratome or a laser. The diseased corneal endothelium is stripped away with surgical instruments and then the lamellar corneal stromal endothelial transplant graft is inserted into the anterior chamber through a full thickness corneal incision. The graft is then held in place against the stripped posterior corneal stromal surface by an air bubble until the graft is able to heal in position.

In both DLEK and DSAEK it is advantageous to be able to insert a relatively large transplant atraumatically through a small corneal or scleral incision. A larger transplant has more corneal endothelial cells and should produce better results in the treatment of corneal endothelial diseases. However, a significant problem with prior art methods of inserting corneal transplants into the anterior chamber through a small incision is that they all involve folding of the transplant and grasping of the transplant with forceps. Moreover, the transplant is typically severely compressed as it passes through the corneal incision. It has been demonstrated through the use of vital staining techniques that many of the delicate corneal endothelial cells of a transplant are killed during the prior art insertion process. Like corneal transplant grafts for DSAEK or DLEK, synthetic corneal implants e.g. corneal inlay prostheses are also very delicate. In many cases, these corneal inlays may be as thin as 30 to 40 microns, which make them very easily torn by forceps. Therefore, there is also a need for an improved method to place these corneal inlays atraumatically through a small incision.

Delivery systems for placement of intraocular lenses (IOLs) into the posterior chamber through a small incision have been described. However, these delivery systems designed for small incision cataract surgery IOLs are not well adapted for use as a delivery system for corneal implants through a small incision. For example, a typical intraocular lens implant may be 1 mm or more in thickness, whereas the typical corneal transplant for DLEK or DSAEK is between 0.1 to 0.15 mm in thickness. Moreover, as has been noted before, the thickness of a corneal inlay prosthesis may be as little as 30 to 40 microns. In addition, the size and shape of an IOL is different from that of a corneal transplant. An IOL is typically 12 to 13 mm in length, 5 to 6 mm wide, and 1 mm or more in thickness, whereas a corneal transplant DSEK graft would typically be circular in shape and would have a diameter of 8 to 9 mm and a thickness from 0.1 mm to 0.2 mm. In the case of a corneal prosthesis implant, the diameter may range from 1 mm to 10 mm and the thickness from 0.01 mm to 0.6 mm. Finally, IOL delivery systems are designed to greatly compress the IOL during the insertion process, whereas this type of compression would be likely to either damage or destroy a living corneal transplant. The amount of compression used for IOL delivery systems could also damage the much thinner corneal implants.

2. Description of the Background Art

Corneal implants and methods for their implantation are described in U.S. Pat. Nos. 4,842,599; 5,112,350; 5,698,192; 5,755,785; 5,843,185; 6,106,552; 6,592,621; 6,814,755; and 7,364,674; and in U.S. Patent Application Publications 2002/0065555; 2003/0014106; 2003/0093066; 2003/0229303; 2005/0080485; 2005/0119737; 2006/0083773; 2006/0134050; 2006/0235428; and 2007/0129797.

BRIEF SUMMARY OF THE INVENTION

Improved systems and methods for implanting corneal implants are provided by the present invention. The phrase "corneal implant" refers to any natural (biological) or synthetic implant or graft that may be implanted into a human cornea. These systems and methods can place a corneal implant through a corneal incision that is substantially less than the width of the implant. The placement of the implant may be within or between any of the layers of the cornea including epithelium, Bowman's membrane, stroma, Descemet's membrane, and endothelium. In preferred aspects, the corneal incision is equal or less than half of the width of the implant. In additional preferred aspects, the system allows the placement of a corneal implant through an incision that is less than or equal to 3 mm, which advantageously avoids the need for suturing of the incision in most cases and also greatly decreases the chance of unwanted induced astigmatism.

In accordance with a first aspect of the present invention, the corneal implant is reversibly deformable in shape to allow its passage through a corneal incision that is equal or less than half of the width of the implant. The corneal implant is bio-compatible with the cornea, the eye, and the body. In certain embodiments, synthetic material which can meet these criteria may potentially be used for the implant. Suitable synthetic materials include one or more compounds selected from the group consisting of collagen, polyurethanes, poly(2-hydroxyethylmethacrylate), polyvinylpyrolidone, polyglycerolmethacrylate, polyvinyl alcohol, polyethylene glycol, polymethacrylic acid, silicones, acrylics, polyfluorocarbons, and polymers with phosphocholine. In other embodiments, the grafts may comprise human corneas harvested for use in transplants such as grafts or DSEK or a graft which consists only of Descemet's membrane and endothelium. Transplantation of only Descemet's membrane and endothelium is referred to as Descemet's Membrane Endothelial Keratoplasty (DMEK). In the future, biological cornea implants may be obtained from other sources such as animals, genetically modified animals, in vitro cell culture, or the like.

In a preferred embodiment, the material comprises a hydrogel. The hydrogel may comprise or consist essentially of collagen, polyurethanes, poly(2-hydroxyethylmethacrylate), polyvinylpyrolidone, polyglycerolmethacrylate, polyvinyl alcohol, polyethylene glycol, polymethacrylic acid, silicones, polyfluorocarbons, and polymers with phosphocholine. Alternatively, the hydrogel may comprise or consist essentially of a material selected from the group consisting of a copolymer of hydroxyethyl methacrylate (HEMA) and methyl methacrylate (MMA). Still further alternatively, the hydrogel may comprise or consist essentially of a copolymer of hydroxyethyl methacrylate (HEMA), methyl methacrylate (MMA), and methacrylic acid. As a still further alternative, the hydrogel may comprise or consist essentially of (a) a multi-network hydrogel with a first network interpenetrated with at least one other network, wherein said first network, said other networks are based on biocompatible polymers and at least one of said network polymers is based on a hydrophilic polymer; (b) epithelization promoting biomolecules covalently linked to the surface of said double network hydrogel; and (c) corneal epithelial cells or cornea-derived cells adhered to said biomolecules.

In an alternative preferred embodiment, the corneal implant is formed from a material comprising of a reversibly deformable acrylic copolymer, such as those used for intraocular lenses. These materials have excellent tensile strength and can be elongated as much as 250% before breaking. Such characteristics allow injection to be performed according to the present invention without damage to the implant. Examples of suitable materials include copolymers of hydroxyethyl methacrylate and methyl methacrylate (e.g. materials available under the tradenames Contamac C126, C118, C121 materials, Benz IOL 25UV and Benzflex 26UV). In additional preferred aspects, the deformable polymer is hydrophilic in nature to allow smooth wetting of the optical surface of the implant. Wetability is an important characteristic of corneal implant which allows the tear film to act as a good optical interface. In yet other preferred aspects the material contains between 1% and 20% methacrylic acid. More preferably 5 to 10% methacrylic acid, which advantageously allows the linkage of tethering molecules such as polyethylene glycol to the surface of the implant. Tethering molecules will allow reactive moieties to be linked to the surface of the implant to create useful implant characteristics such as promotion of epithelialization or the ability to create chemical bonds with the cornea. Other preferred physical characteristics of the corneal implant material would be a tensile strength in the range of 0.1 to 4 MPa, more preferably a tensile strength in the range of 0.6 to 2.6 MPa. In addition, a modulus of 0.1 to 5 MPa, more preferably a modulus in the range of 0.2 to 3.1 MPa would also be desirable. Although we have described specific types of acrylic copolymers as suitable for corneal implants, other types of materials (e.g. silicone or collagen polymers) which have similar physical and chemical characteristics as those described above could also be used and are all considered part of the present invention.

In other preferred embodiments, holes or pores may be provided in the implant to increase biocompatibility of the implant by allowing nutritive substances and gasses (e.g., water, glucose, and oxygen) to pass easily through the implant in order to maintain healthy metabolism in the cornea. In still other preferred embodiments, the polymer material may have thermoplastic properties such that the implant will have one desired shape at one temperature and then deform into another desired shape at a second temperature. In yet other preferred aspects, the corneal implant may comprise one or more separate, smaller components that can be assembled in situ placed inside the corneal pocket. Such in situ assembly advantageously minimizes the incision size needed to insert a corneal implant.

The corneal implant may be of any shape that allows it to be placed within a corneal pocket. In preferred embodiments, the corneal implant is substantially round. In alternate preferred embodiments, the corneal implant is not round. A corneal implant which is not round has the advantage that it is less likely to rotate within a corneal pocket. This property is useful in the implants which correct for astigmatism.

In preferred other embodiments, the corneal implant is a lens. The lens can be a monofocal, multifocal, Fresnel, diffractive, prismatic, or other type of lens that can be used to treat refractive error (such as myopia, hyperopia, or astigmatism) presbyopia, or ocular disease e.g. macular degeneration. The lens may also be made of a polymer that can have its refractive properties adjusted permanently or reversibly by electromagnetic energy as described in U.S. Patent Application 2003/0173691 to Jethmalani.

The corneal implant may comprise a prosthesis that is used to replace or augment a portion of the cornea. Such implants are useful in restoring optical clarity or structural integrity to the cornea in lieu of corneal transplantation. The corneal prosthesis may be used to replace only a partial thickness portion of the cornea or a full thickness portion of the cornea. In preferred aspects, the corneal implant may be coated with extracellular matrix proteins such as collagen, fibronectin, laminin, substance P, insulin-like growth factor-1, or peptide sequences such as fibronectin adhesion-promoting peptide (FAP). In additional preferred aspects, these extracellular matrix proteins and peptides are tethered or otherwise bound to the epithelial side of the corneal implant by the methods described in U.S. Pat. No. 6,689,165, to Jacob et al. Such surface treatments are intended to promote epithelialization on the surface of a corneal implant.

In alternate preferred embodiments, the surface of the corneal implant may have a texture that promotes epithelialization on the surface of the corneal implant. Textures, such as surface indentations, may be applied to the surface of the corneal implant to promote epithelialization, as described in U.S. Pat. No. 6,454,800 to Dalton et al.

In yet other alternate preferred embodiments, the corneal implant may be manufactured from a material that promotes epithelialization on the surface of the corneal implant. Examples of such materials include polymers selected from the group consisting of collagen and N-isopropylacrylamide, collagen and 1-ethyl-3.3'(dimethyl-aminopropyl)-carbodiimide as well as collagen and N-hydroxysuccinimide (EDC/NHS). In further preferred aspects, the polymer may additionally contain extracellular matrix proteins such as fibronectin, laminin, substance P, insulin-like growth factor-1, or peptide sequences such as fibronectin adhesion-promoting or peptide (FAP).

Optionally, at least a portion of the device may contain holes or be porous in nature so as to promote growth of corneal tissue into and through the implant in order to promote retention and biocompatibility. Such porous implants may be fabricated as described in U.S. Pat. No. 6,976,997 to Noolandi et al. and U.S. Pat. No. 5,300,116 to Chirila et al.

Optionally, at least a portion of the lens or other corneal implant may be colored. Coloration can be useful for cosmetic purposes or for therapeutic purposes e.g. treatment of aniridia. For example, methods of applying biocompatible inks, which are well known in colored contact lens manufacturing, may be used to color the corneal implant. Particular coloring methods are described in U.S. Patent Applications 2003/0054109 and 2003/0025873, the disclosures of which are incorporated herein by reference. In alternate preferred aspects, the corneal implant may be colored with photosensitive inks that change color with exposure to electromagnetic waves. This allows the color of the corneal implant to be adjusted permanently or reversibly by exposure to electromagnetic waves in vivo.

Optionally, the corneal implant may also contain an ultraviolet filter compound of the benzophenone type such as 3-(2 Benzyotriazolyl)-2-Hydroxy-5-Tert-Octyl-Benzyl Methacryl Amide.

In alternate preferred embodiments the corneal implant may comprise a scaffold having a three-dimensional structure including discrete elements defining a peripheral shape with a mostly empty interior volume therein. The predetermined shape is selected to provide a vision correction when placed in a corneal pocket. The scaffold can be inserted into a corneal pocket for the purpose of reshaping or supporting the cornea.

Reshaping of the cornea is useful for correction of various vision problems including refractive errors as well as for the treatment of ectactic corneal disorders such as keratoconus or pellucid marginal degeneration. In preferred aspects the corneal implant scaffold consists of a three dimensional structure where it is not possible for a single plane to pass through all of the elements of the structure. In other preferred aspects the corneal implant scaffold is reversibly deformable so that it may be introduced to a corneal packet by the devices and methods of the present invention. Also preferably, the corneal implant scaffold should have a rigidity that is greater than a mammalian cornea, so that insertion of the scaffold into a corneal pocket will result in either a change in shape of the cornea or be able to provide increased structural strength to the cornea.

In preferred aspects of the present invention, the tensile strength of the material used to make the corneal scaffold implant should be in the range between 2.5 MPa and 53 GPa and the Young's modulus between 3 MPa to 5 TPa More preferably, a tensile strength in the range between 800 to 2000 MPa and a Young's modulus between 25 to 100 GPa.

In other preferred aspects, the corneal implant scaffold is made of a biocompatible and reversibly deformable polymer or a biocompatible and reversibly deformable metal or alloy (e.g. gold, titanium, nickel titanium alloy, copper-zinc-aluminum-nickel alloy, and copper-aluminum-nickel alloy). In yet other preferred aspects, the corneal scaffold is made from a fullerene including, but not limited to carbon nanotubes, spheres, ellipsoids, planes, or ribbons. In additional preferred aspects the width of the structural elements in the corneal implant scaffold is 0.001 mm to 1 mm, more, preferably 0.3 to 0.6 mm. In preferred aspects the thickness of the structural elements in the scaffold is 0.001 mm to 0.5 mm, more preferably 0.01 mm to 0.06 mm. In alternate preferred aspects the cornea scaffold implant may also include a lens within the structure, which advantageously combines correction of refractive error by both changing of the shape of the cornea and the addition of another lens. The cornea scaffold may be shaped in ways to correct for myopia, hyperopia, astigmatism, and presbyopia. For example a shape which flattens the central cornea will correct for myopia. A shape which steepens the central cornea will correct for hyperopia. A shape which flattens the central cornea and flattens the steep axis of the cornea will correct for myopia and astigmatism. A shape that steepens the central cornea and flattens the steep axis of the cornea will correct for hyperopia and astigmatism. A shape that produces multifocality of the cornea will correct for presbyopia. Examples of shapes which can correct for presbyopia include a shape which steepens the central cornea while keeping the peripheral corneal shape the same or a shape which steepens the peripheral cornea while keeping the central corneal shape the same.

A scaffold corneal implant has a number of advantages compared to a corneal implant which is mostly solid. For example if a high degree of refractive correction is desired, a centrally located solid corneal implant will need to be fairly thick. A relatively thick solid corneal implant will decrease the permeability of essential nutrients and gases to the anterior and posterior to the implant. Lack of normal nutrient and gas transport could result in undesirable consequences such as melting or necrosis of the corneal tissue. In contrast, a thin scaffold implant can correct large amounts of refractive error without significantly interfering with corneal physiology because most of the implant is empty space. Moreover, because the scaffold corneal implant is mostly empty space, the scaffold corneal implant can be made to be highly compressible which can allow for insertion through a smaller incision and thereby decrease recovery time for the patient.

In yet other alternate preferred embodiments, the corneal implant may be a device. Examples of potential implant devices include miniature cameras and aqueous glucose monitors.

The improved corneal implants of the present invention are reversibly deformable into a reduced width shape that allows passage through a corneal incision that is substantially less than the width of the implant when not deformed or unconstrained. In preferred aspects, the implant will be insertable through an incision that is less than or equal to one-half of the width of the implant, preferably being 3 mm or less.

A specific reversibly deformable corneal implant according to the present invention comprises a center optic having an anterior surface, a posterior surface, and a peripheral wall. The implant further includes at least one rim circumscribing at least a portion of the peripheral wall. In contrast to the rigid implants and lenses of the prior art, at least the rim of the corneal implant of the present invention will be radially compressible to allow the implant to be radially constrained for insertion into a corneal pocket or opening. Usually, the center optic and the rim will comprise a monolithic structure, i.e. a structure which is substantially continuous and free from discontinuities throughout. Such monolithic structures may be formed by molding, machining a block of material, or other conventional corneal implant fabrication techniques. The preferred materials will be the hydrogel materials listed hereinbefore.

In a first specific embodiment of this corneal implant, the implant will comprise or consist essentially of a single rim circumscribing the center optic at a location intermediate the anterior and posterior surfaces. Usually, but not necessarily, the peripheral wall will be oriented at an angle in the range from 1° to 144° relative to plane which intersects the junction of the rim and the peripheral wall anterior to the rim, i.e. toward the external end of the implant when it is implanted in a cornea. The center optic will usually have a peripheral wall diameter in the range from 3 mm to 8 mm and a thickness in the anterior-posterior direction in the range from 0.1 mm to 3 mm. The rim will have a width, typically a diameter, greater than the diameter of the peripheral wall, usually being in the range from 3.5 mm to 12 mm. The geometry of the rim will usually be circular, but could also be oval, polygonal, or irregular, usually having a concave profile in the posterior direction.

In an alternative embodiment, the corneal implant will comprise at least an anterior rim circumscribing at least a portion of the peripheral wall at or near the anterior surface of the center optic and a posterior rim circumscribing at least a portion of the peripheral wall at or near the posterior surface of the center optic. The rims will both be sufficiently resilient and collapsible so that they may be compressed against the center optic to permit and facilitate implantation of the implant within the cornea. With the two-rimmed implant, implantation will usually be in an anterior-posterior direction through a hole or aperture formed entirely through the center of the cornea, where the anterior rim acts as a flange or retaining element, engaging the upper surface of the cornea, and the posterior rim also acts as an anchor or retaining element engaging the interior surface of the cornea.

The implant embodiments having both anterior and posterior rims, the center optic will typically be cylindrical with a peripheral wall diameter in the range from 3 mm to 9 mm and a thickness in the anterior-posterior direction in the range from 0.1 mm to 1.2 mm. The anterior and posterior rim diameters may be the same or different, always being larger than the adjacent cylindrical wall diameter, typically being in the range from 3.5 mm to 9 mm. The anterior and posterior rims will usually have circular peripheries and convex, conical, or otherwise tapered anterior surfaces, but it will be appreciated that other peripheral geometries could be employed as well.

A system according to the present invention comprises a hollow member and implant mover or other axial pusher used to deliver a corneal implant that has been constrained to fit inside an axial hollow passage of the hollow member. The implant may be deformed or constrained in any shape or configuration having a "reduced width" that allows it to be fit inside of the hollow member e.g., rolled or folded. By "reduced width" it is meant that a maximum width of the implant, such as a diameter of a circular lens, is reduced by some threshold amount, typically by at least one-half (50%), often by at least 60%, and sometimes by 65% or more.

A system according to the present invention comprises a hollow member and implant mover used to deliver a corneal implant that has been restrained to fit inside of the hollow member. Once the corneal implant is inside the hollow member, the implant mover is used to move the implant into a corneal pocket or the anterior chamber.

Optionally, the system may further comprise a deformation chamber where the implant is deformed into a shape and size that will fit inside the hollow member. In preferred aspects, the deformation chamber may contain ridges, protrusions, indentations, or recesses which help to maintain and guide the orientation of the corneal implant within the deformation chamber during the deformation process. In further preferred aspects the deformation chamber will be a size that is appropriate for the type of corneal implant which is being used. For example in the case of a corneal transplant, the minimum internal dimensions of an open deformation chamber should be between 6 and 10 mm, more preferably between 8 and 9 mm. In the case of a corneal implant prosthesis, the minimum internal dimensions of an open deformation chamber dimensions should be between 1 mm and 10 mm, more preferably between 2.0 mm and 7 mm. In additional preferred aspects the deformation area may be tapered or funnel shaped, i.e. narrower one end than on the other end. The tapered or funnel shape advantageously facilitates the corneal implant to be restrained to a smaller diameter configuration.

In other preferred aspects, the interior of the hollow member may contain ridges, protrusions, indentations, or recesses which help to maintain and guide the orientation of the corneal implant as it travels inside of the hollow member.

Such surface features will be arranged to prevent rotation of the corneal implant during insertion which might otherwise disorient the implant within the pocket. In additional preferred aspects, the interior of the hollow member may contain ridges, protrusions, indentations, or recesses which guides a lamellar corneal stromal endothelial transplant to deform in a way which allows it to travel through a small incision without the need for folding or being grasped by forceps. The system is designed to allow a corneal transplant to be placed through an incision equal or less than 3 mm. However, the system can also be used to place an implant through an incision that is greater than 3 mm.

Optionally, the system may be designed to be sterile and disposable for single use. This advantageously decreases the chance for contamination and infection. It also obviates the need for the surgeon to autoclave or to provide other methods of sterilization such as ethylene oxide. To insure that the system will be both sterile and single use only we can add one or more of the following features. In preferred aspects one or more components of the system may be made of a polymer which will melt or deform into an unusable shape upon autoclaving. In additional preferred aspects, the system may have a one way locking mechanism, such that once the tip of the implant mover travels to a certain distance, the implant mover is locked in position inside of the hollow member, thus preventing reloading of another corneal implant. In alternative preferred aspects, the system may be assembled through the use of breakable tabs or snaps, which allows the secure assembly of the disposable component, but which are easily destroyed if there is an attempt to disassemble the system for reuse.

Optionally, the system may be designed so that the corneal implant is pre-loaded inside of the hollow member prior to use by the surgeon. This advantageously minimizes the need for manipulation of the delicate corneal implant by the surgeon, which could result in damage to the corneal implant.

Once the corneal implant is inside the hollow member, the implant mover or other axial pusher is used to engage and push the implant into the corneal pocket. Optionally, the system may further comprise a deformation chamber where the implant is deformed into a shape and size that will fit inside the hollow member. In other preferred aspects, the deformation chamber may contain ridges, protrusions, indentations, or recesses which help to maintain orientation of the corneal implant within the deformation chamber during the deformation process. Optionally, the hollow member is tapered, i.e., narrower at a distal end than at a proximal end. Such tapering allows additional deformation (size or width reduction) of the implant as it is advanced through the hollow member and passes out through a smaller distal opening. The interior of the hollow member may contain ridges, protrusions, indentations, or recesses which help to maintain orientation of the corneal implant as it travels inside of the hollow member. The system for implant placement is designed to allow an implant to be placed into a corneal pocket with an entry incision that is equal or less than one-half of the width of the implant, however, the system can also be used to place an implant through a corneal incision that is greater than one-half of the width of the implant.

The present invention further provides methods for delivering a corneal implant to a cornea. A first exemplary method comprises forming a central anterior opening in the cornea. The implant is introduced through the opening, where the implant includes a center optic and a peripheral rim wherein the peripheral rim is constrained while being introduced. After introduction, the peripheral rim is released from constraint so that the peripheral rim radially expands to engage corneal tissue circumscribing the central anterior opening, where the rim helps anchor the implant in place.

Forming the central anterior opening may comprise creating an opening extending from an anterior corneal surface through the full thickness of the cornea. Alternatively, the opening may be only partial extending from the anterior surface only part way through the thickness of the cornea.

In a first exemplary embodiment of the method of the present invention, the implant is introduced in a posterior direction into the central anterior opening, where the peripheral wall of the central anterior opening remains intact, i.e. there are no lateral openings formed into the central anterior opening. Alternatively, introducing the implant may comprise forming a pocket through a lateral opening in the cornea, wherein the implant is introduced through the lateral opening into the pocket and from the pocket into the central anterior opening.

Using either introductory protocol, the corneal implant may have a single rim about a mid-sectional region of the center optic, where the rim extends into corneal tissue circumscribing the central anterior opening after it is released from constraint. In other alternative embodiments, the corneal implant may have an anterior rim and a posterior rim, as described generally above, where the anterior rim radially expands over an anterior corneal surface circumscribing the central anterior opening and the posterior rim radially expands over a posterior corneal surface circumscribing the central anterior opening.

In further preferred aspects of the method of the present invention, the center optic will be less compressible than the rim so that the center optic is not substantially compressed as the implant is being introduced. In other embodiments, both the rim and the center optic may be compressible and compressed while the implant is being introduced.

In preferred aspects of the methods of the present invention, the corneal implant will be introduced by advancing the implant through a tube having a width which compresses at least the rim of the implant, where the implant is released as it is advanced out of the tube, in turn releasing the rim to expand and engage the corneal tissue. The tube is preferably tapered in a distal direction so that it progressively compresses the rim before the implant is released from the tube.

BRIEF DESCRIPTION OF THE DRAWINGS

FIGS. 2A through 2C illustrates a first embodiment of apparatus of the present invention.

FIGS. 3A through 3C illustrate side views of a corneal implant as it is advanced and constrained by the apparatus of FIGS. 2A-2C.

FIGS. 6A through 6C illustrate a third embodiment of the apparatus of the present invention.

FIGS. 7A and 7B illustrate use of the apparatus of FIGS. 6A-6C in implanting an implant in a cornea.

FIGS. 9A through 9F illustrate a further implantation protocol in accordance with the present invention.

FIGS. 10A through 10F illustrate a further implantation protocol in accordance with the present inventions.

FIGS. 11A through 11F illustrate a further implantation protocol in accordance with the present inventions.

FIGS. 12A and 12B illustrate a tool in accordance with the principles of the present invention for collapsing and advancing a corneal implant.

FIGS. 13A and 13B illustrate an alternative tool in accordance with the principles of the present invention for collapsing and advancing a corneal implant.

FIGS. 14A and 14C are cross-sectional views of the tool of 13A and 13B showing the implant as it is advanced as shown in FIGS. 15A through 15D.

FIGS. 15A through 15D illustrate use of the tool of FIGS. 13A and 13B for advancing and reducing the cross-section of an implant in accordance with the principles of the present invention.

FIGS. 16 A-F illustrate an alternative tool in accordance with the principles of the present invention for collapsing and advancing a corneal implant.

FIGS. 17 A-C illustrate a corneal scaffold embodiment of the corneal implant for the treatment of myopia.

FIGS. 18A-B illustrate a corneal scaffold embodiment of the corneal implant for the treatment of hyperopia.

FIGS. 19 A-B illustrate a corneal scaffold embodiment of the corneal implant for the treatment of hyperopic astigmatism.

FIGS. 20 A-B illustrate a corneal scaffold embodiment of the corneal implant which also includes a lens.

DETAILED DESCRIPTION

Figure 1A:
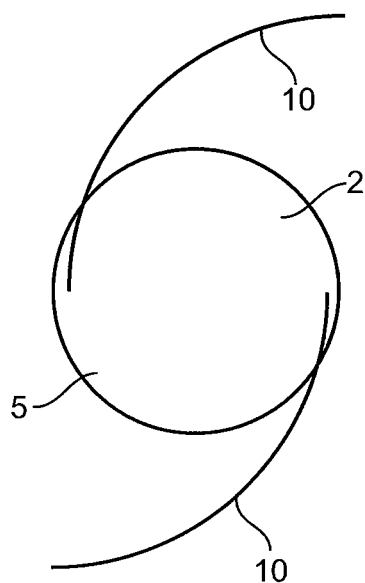
FIGS. 1A, 1B, 1C, and 1D illustrate prior art corneal implants.
Figure 1B:
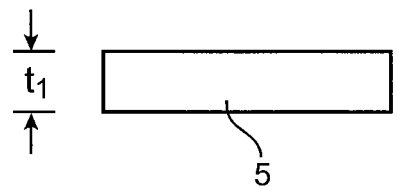
Figure 1C:
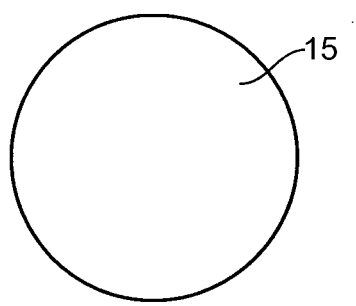
Figure 1D:
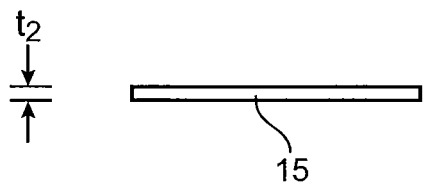

FIG. 1A shows a top view of a cataract surgery lens implant 2. A round optic 5 of the implant 2 has haptics 10 which extend from the periphery of the optic. The haptics 10 are used to help the optic center and fixate within the capsular bag. FIG. 1B shows a side view of a cataract surgery lens implant optic 5. Note that the thickness $t_1$ of the optic 5 is typically 1 mm or more and is substantially greater than the 0.5 to 0.6 mm thickness of the human cornea. The thickness of the optic 5 makes it inappropriate for use as a corneal lens implant. FIG. 1C shows a top view of a corneal implant 15. Note there are no haptics on the corneal implant. FIG. 1D shows a side view of corneal implant 15. Note that the thickness $t_2$ is substantially less than cataract surgery lens implant 5. The thickness $t_2$ of corneal implant 15 would in general be less than the thickness of the human cornea.

FIG. 2A shows a corneal implant delivery system 18 in partial section. A hollow member 20 having a distal tip 21 (which is preferably beveled or chamfered) defines hollow axial passage 25 (e.g. an axial lumen). Axial pusher 30 has a tip 35 that engages a corneal implant 15 that has been deformed in shape and constrained to fit inside the hollow axial passage 25 of the hollow member 20, as shown in FIG. 2B. The cross-section of hollow passage 25 may be circular, polygonal, or any other shape that is conducive to constraining the corneal implant 15. The hollow axial passage 25 of the hollow member 20 may contain ridges, protrusions, indentations, or recesses (now shown) which help to maintain orientation of the corneal implant as it advances distally of the hollow member (not shown). Axial pusher 30 engages one end of the constrained corneal implant 15 to advance the constrained implant through hollow passage 25. FIG. 2C shows the constrained corneal implant 15 emerging from a distal end of the hollow passage 25 still in its deformed and constrained configuration. By placing the tip of the hollow member 20 through an incision in the cornea, the corneal implant 15 may be advanced into the corneal pocket (not shown) through even a very small incision. In preferred aspects, the corneal implant is able to pass through an entry incision that is less than one-half the width of the corneal implant. In those cases, the hollow member will have an external width from 0.5 mm to 5 mm, preferably from 1 mm to 3 mm and an internal width from 0.3 mm to 4.8 mm, preferably from 0.8 mm to 2.8 mm.

FIG. 3A shows a side view of corneal implant 15 in its non-deformed, non-constrained shape. FIGS. 3B and 3C shows an end on view of the corneal implant 15 as it is moved within the hollow member 20. Note that the corneal implant 15 has been deformed and constrained into a rolled configuration. The rolled configuration will preferably have a diameter in the range from 0.3 mm to 4.8 mm, more preferably from 0.6 mm to 2.6 mm, to fit into the hollow passage 25 of the hollow member 20.

Figure 4A:
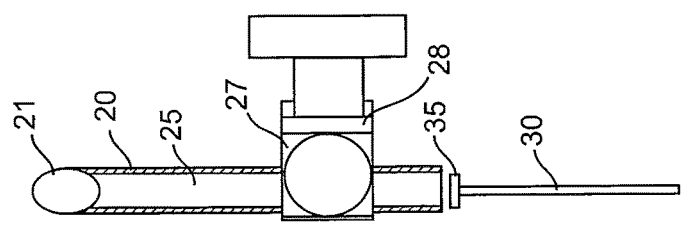
FIGS. 4A through 4D illustrate a second embodiment of the apparatus of the present invention.
Figure 4B:
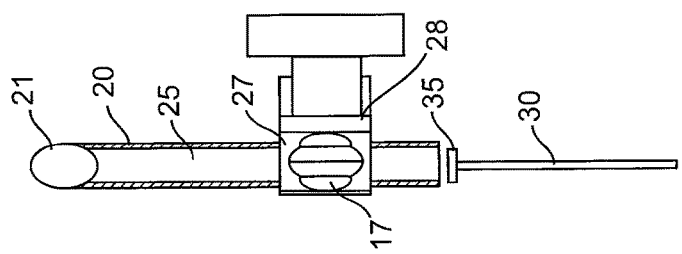
Figure 4C:
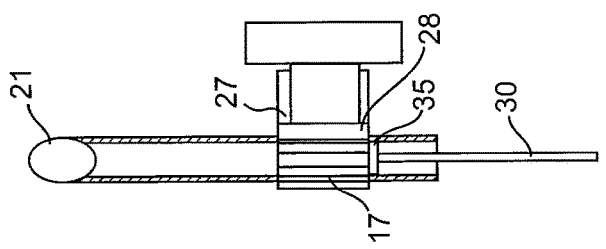
Figure 4D:
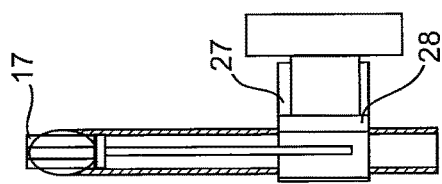
Figure 5A:
FIGS. 5A through 5D illustrate side views of a corneal implant as it is advanced and constrained by the apparatus of FIGS. 4A-4D.
Figure 5B:
Figure 5C:
Figure 5D:

FIG. 4A-4D shows a corneal implant delivery system with a deformation chamber 27 and a deforming member 28. In this embodiment of the invention, the corneal implant 15 is placed into the chamber 27 in an unconstrained and not deformed configuration and is then deformed into a folded or rolled corneal implant 17 within deformation chamber 27 by deforming member 28. Deforming member 28 is moved within deformation chamber 27 to deform and fold corneal implant 15 into a folded or rolled corneal implant 17. FIG. 4C shows axial pusher 30 engaging deformed corneal implant 17 by implant mover tip 35. FIG. 4D shows deformed and folded corneal implant 17. Axial pusher 30 engages corneal implant 17 to push the deformed constrained implant inside hollow passage 25. FIG. 4D shows that corneal implant 17 has been advanced by axial pusher 30 out of the hollow passage 25 while retaining a constrained shape. The constrained configuration of corneal implant 17 allows passage into the corneal pocket (not shown) through a small incision. The presence of the optional deformation chamber 27 and deforming member 28, advantageously allows the corneal implant 15 to be easily deformed into a configuration that will allow it to be placed through a small corneal incision into a corneal pocket.

FIGS. 5A-5D show side views of the corneal implant 15 being deformed into an exemplary deformed and folded or pleated corneal implant 17.

FIGS. 6A-6C show a top view of an alternative corneal implant delivery system 100. In this embodiment a corneal implant 115 is placed into a deformation area 122. When the "wings" 123 of the deformation area are closed, a deformation chamber 124 (FIG. 6B) is formed which deforms the corneal implant 115. In this embodiment, the corneal implant 115 is folded in half A tip 132 of an axial pusher 130 engages corneal implant 115. The hollow member 120 is tapered so that hollow passage 126 is narrower at a distal end 121 that inserts into the corneal pocket. This allows the corneal implant 115 to be deformed into an even smaller cross-section as the implant is advanced distally and through the distal end 121. Advantageously in this embodiment, the implant mover tip 132 may also be deformable to fit within the narrowing hollow passage 126.

FIG. 7A shows a side cross-sectional view of corneal implant 115 being inserted into corneal pocket 140. FIG. 7B shows the final shape of corneal implant 115 after it has been inserted into corneal pocket 140 and unfurled or otherwise expanded back to its unconstrained size within cornea 145.

Figure 8A:
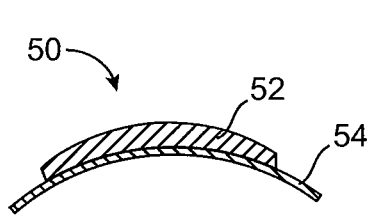
FIGS. 8A through 8F illustrate preferred corneal implants in accordance with the present invention.
Figure 8B:
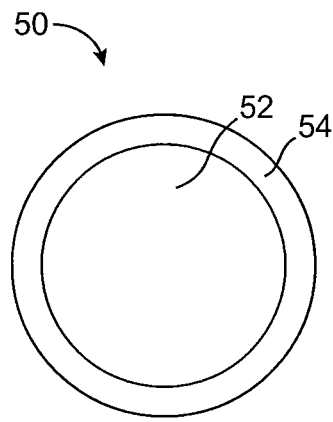

FIG. 8A illustrates a cross-sectional view of a corneal implant prosthesis 50 Corneal implant 50 is meant to replace a portion of the anterior layers of the cornea. In this embodiment there is a central optic 52 that protrudes anteriorly from a rim 54. In preferred aspects, the central optic would protrude anteriorly from the rim by 1 to 600 microns. More preferably, the central optic would protrude anteriorly from the rim by 50 to 400 microns. The central optic 52 will replace diseased anterior corneal tissue that has been removed. The rim 54 is designed to partly or fully surround the center of optic and to fit within the peripheral recesses of a corneal pocket in order to anchor the corneal implant prosthesis to the cornea. The rim may be a continuous skirt as illustrated or may be crenellated or otherwise distributed in sections about the periphery of the center optic. FIG. 8B shows a top view of corneal implant prosthesis 50 which shows the central optic 52 and the rim 54. The rim 54 may optionally contain holes or be porous in nature so as to promote growth of corneal tissue into and through the implant, in order to promote retention and biocompatibility.

Figure 8C:
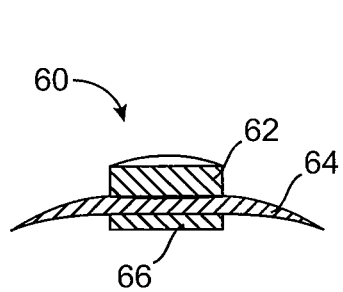
Figure 8D:
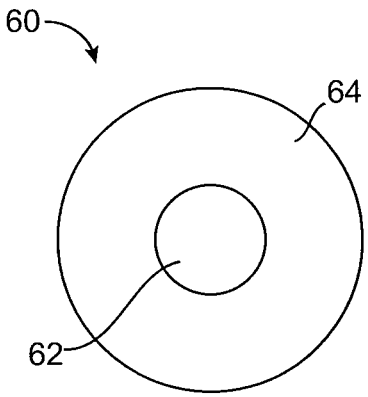

FIG. 8C shows a cross-sectional view of corneal implant prosthesis 60 which is meant to replace a full-thickness area of the cornea. FIG. 8D shows a top view of the same implant prosthesis 60. In this embodiment there is an anterior portion of central optic 62 which protrudes anteriorly from a rim 64. The anterior portion of central optic 62 will replace diseased anterior corneal tissue that has been removed. In preferred aspects, the central optic would protrude anteriorly from the rim by 1 to 600 microns. More preferably, the central optic would protrude anteriorly from the rim by 50 to 400 microns. In addition corneal implant prosthesis 60 has a posterior portion of central optic 66 which protrudes posteriorly from rim 64. In preferred aspects, the central optic would protrude posteriorly from the rim by 1 to 900 microns. More preferably, the central optic would protrude posteriorly from the rim by 50 to 800 microns. The posterior portion of central optic 63 will replace diseased posterior corneal tissue that has been removed. The rim 64 will anchor corneal implant prosthesis 60 within the peripheral recesses of the corneal pocket and provide a water-tight seal. The rim 64 may optionally contain holes or be porous in nature so as to promote growth of corneal tissue into and through the implant, in order to promote retention and biocompatibility. The rim may be formed from any of the lens materials described above.

Figure 8E:
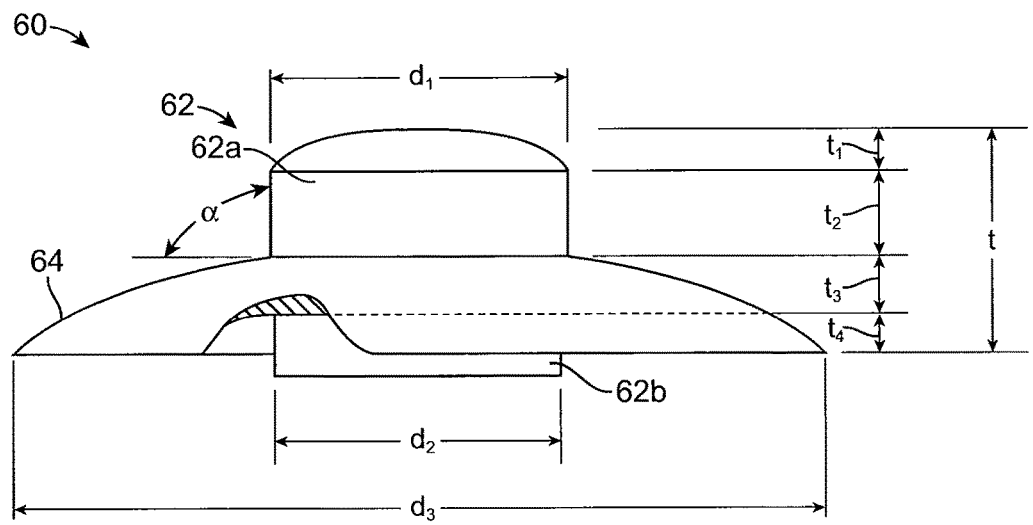

FIG. 8E is an enlarged view of the reversibly deformable implant prosthesis 60 shown in FIGS. 8C and 8D. The center optic 62 includes a protruding anterior optic 62a and optionally a protruding posterior optic 62b. The rim 64 surrounds the center optic 62 and defines said anterior and posterior protruding optics 62a and 62b. Preferably, the implant prosthesis 60 is formed as an integrated or monolithic structure and is free from discontinuities, joints, adhesions, connections, and other fabrication artifacts. In a specific aspect, the sidewall of the anterior protruding optic 62a is disposed at an angle α relative to the plane which intersects the junction of the rim in the anterior optic between 1° and 144°. The diameter $d_1$ of the anterior optic is preferably between 3 mm and 9 mm, while the diameter $d_2$ of the posterior optic is also between 3 mm and 9 mm, although the two diameters are not necessarily equal. The diameter $d_3$ of the rim will usually be substantially greater than that of either of the optics, typically being in the range from 3.5 mm to 12 mm.

The anterior surface of the center optic will typically be curved, more typically being generally spherical with a radius in the range between about 3 mm and 4 mm. The anterior surface of the rim 64 will usually be conical or generally spherical, with spherical surfaces having a radius generally in the range between 1.5 mm and 9 mm, and often being the same as that of the anterior surface of the anterior optic 62a. The posterior surface of the rim 64 will also generally be conical or spherical, typically being spherical with a radius in the range from about 1.5 mm to about 9 mm. The posterior face of the posterior optic 62b may be planar or have a radius in the range from 1.5 to 9 mm. The total thickness t of the center optic 60 will typically be in the range from 0.1 mm to 3 mm, with $t_1$ being in the range from 0.01 mm to 0.15 mm, $t_2$ being in the range from 0.05 mm to 1.1 mm, and $t_3$ being in the range from 0.05 mm to 0.5 mm, and $t_4$ being in the range from 0 mm to 2 mm.

Figure 8F:
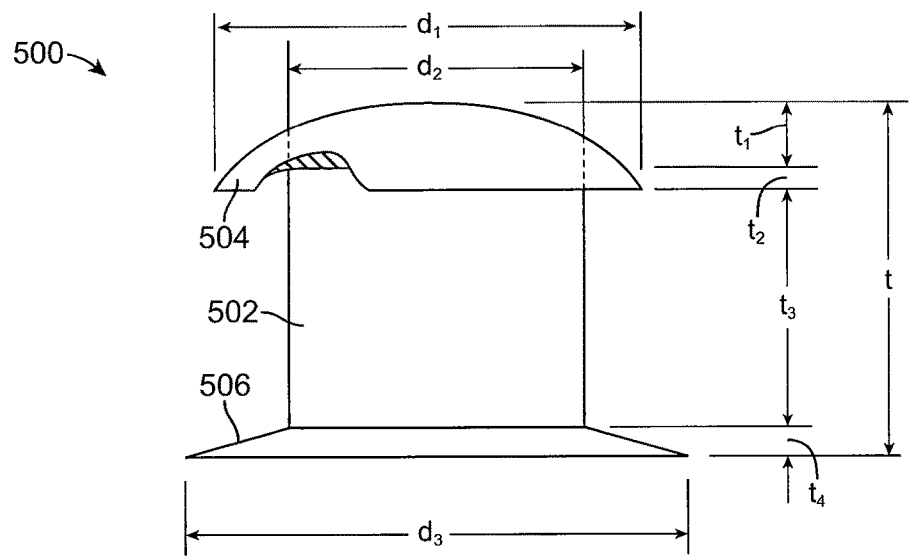

Referring now to FIG. 8F, a further corneal prosthesis 500 constructed in accordance with the principles of the present invention, comprises a center optic 502 having an anterior rim 504 and a posterior rim 506. At least the anterior rim 504 and posterior rim 506 are sufficiently flexible so that they may be collapsed upon introduction into a corneal opening or pocket when introduced in accordance with the methods of the present invention. Often, the center optic 502 will also be compressible. The corneal implant 500 will typically be molded, cast, machined from a single material and will be free from discontinuities and artifacts of fabrication as discussed above with respect to the implant 60. Corneal implant 500 will typically have a total thickness t which is sufficient for implantation in the cornea to span the full thickness of the cornea, typically being in the range from 0.1 mm to 3 mm. The thickness $t_1$ of the anterior rim 504 between the top of the center optic 502 and the top of the rim is in the range from 0.001 mm to 0.3 mm, while the bottom of the anterior rim is recessed by a distance $t_2$ in the range from 0 mm to 0.3 mm. The center optic between the anterior rim and the top of the posterior rim 506 will typically have a length $t_3$ in the range from 0.1 mm to 1.2 mm, while the posterior rim 506 will have a thickness $t_4$ in the range from 0.01 mm to 2 mm.

The center optic 502 of the implant 500 will typically be cylindrical and have a diameter selected to correspond to the diameter of the opening formed in the cornea, although often the diameter when the implant is fully hydrated will be slightly greater than that of the opening. Usually, the diameter $d_2$ of the center optic 502 will be in the range from 3 mm to 9 mm. The widths of the anterior rim 504 and the posterior rim 506 will be greater than the diameter of the center optic 502 since the rims will be holding the center optic in place. Typically, the rims 504 and 506 will have circular geometries, although a variety of other shapes could be used, with the anterior rim having a diameter $d_1$ in the range from 3.5 mm to 12 mm and the posterior rim having a diameter $d_3$ in the range from 3.5 mm to 12 mm. Methods for introducing the implant 500 into a corneal opening are described in more detail below with reference to FIGS. 21A-21C.

FIGS. 9A-9F show a method of treating an anterior corneal disease process using the methods and apparatus of the present invention. In each FIG. 9A-F, a cross-sectional view of the cornea is seen above and a top view is seen below. In FIG. 9A it is shown that pocket 40 has been created posterior to anterior diseased cornea 43. FIG. 9B shows that anterior diseased cornea 43 has been excised with a circular trephine (not shown) to create an open top having a peripheral pocket. The edge of the excision is shown as 45. FIG. 9B also shows corneal implant 50 resting in the deformation area 122. In FIG. 9C the hollow member 120 has been inserted into pocket 40 through external opening 42 and corneal implant 50 has been folded in half within deformation chamber 124. FIG. 9D shows that corneal implant 50 has been further deformed into a more compact shape by its movement through narrowing hollow passage 126 and is being extruded into pocket 40. FIG. 9E shows that corneal implant 50 has been restored to its original shape within corneal pocket 40. Central optic 52 fills the space left by excised diseased anterior cornea 43 and restores optical clarity to the cornea. Hollow member 120 and implant mover 30 have been withdrawn from corneal pocket 40. FIG. 9F shows the final appearance of corneal implant 50 fixated within corneal pocket 40.

FIGS. 10A-10F show a method of treating a full-thickness corneal disease (e.g. pseudophakic bullous keratopathy) through the use of the present invention. In each FIG. 10 A-F, a cross-sectional view of the cornea is seen above and a top view is seen below. In FIG. 10A it is shown that pocket 40 has been created within the layers of the diseased cornea 41. The pocket divides the cornea into diseased anterior cornea 43 and diseased posterior cornea 44. FIG. 10B shows that anterior diseased cornea 43 has been excised with a circular trephine (not shown). The edge of the excision is shown in dashed lines as 45. The opening in the anterior cornea within the edge of the excision 45 is shown at reference number 46. FIG. 10B also shows corneal implant 60 resting in the deformation charter or area 122. In FIG. 10C the hollow member 120 has been inserted into pocket 40 through external opening 42 and corneal implant 60 has been folded in half within deformation chamber 122. FIG. 10D shows that corneal implant 60 has been further deformed into a more compact shape by its movement through narrowing hollow passage 126 and is being extruded into pocket 40. FIG. 10E shows that corneal implant 60 has been restored to its original shape within corneal pocket 40. Anterior optic 62 fills the space left by the excised diseased anterior cornea 43. In preferred aspects, after corneal implant 60 has been positioned in the pocket, the posterior diseased cornea 44 can be excised with low profile curved corneal scissors or some other cutting tool (e.g. plasma blade) inserted through external opening 42. FIG. 10F shows the final appearance of corneal implant prosthesis 60. Note that the rim 64 anchors corneal implant prosthesis 60 within the peripheral recesses of the corneal pocket and provides a water-tight seal. In this embodiment, posterior optic 63 protrudes through the space left by excised diseased cornea 44. However, posterior optic 63 is optional and is not necessarily required for the corneal implant to properly function. It is to be understood that the relative dimensions, shapes, and angles of the anterior central optic 62, posterior central optic 63, and rim 64, may each be modified to promote improved retention as well as optical qualities all in keeping within the scope of the present invention.

In alternative preferred aspects, the corneal implant 60 may be introduced into the pocket 40 using the injector system as described previously in FIGS. 9 and 10 through an opening 46. The hollow member 120 may be inserted through the opening 46, and the corneal implant 60 then injected into the pocket 40. In yet other alternative preferred aspects, the corneal implant 60 may be placed into the pocket 40 by constraining the corneal implant 60 into a small diameter configuration (e.g. with forceps) and inserting it through the opening 46 into the pocket 40 without the use of the hollow member 120 (not shown).

FIG. 11A-11F show an embodiment of a corneal implant that can be assembled within the corneal pocket. By assembling individual smaller pieces of the corneal implant within the corneal pocket, a relatively large corneal implant can be constructed while using a relatively small external incision. The top portion of FIGS. 11A and 11B show a cross-sectional view of a cornea with an intra-stromal pocket. The bottom portion of FIG. 11A shows a top down view of a cornea with an intra-stromal pocket. In both FIGS. 11A and 11B, it can be seen that the first half of the rim 70 has already been inserted inside the pocket. A second half of the rim 74 is being inserted through the small external incision. Note that because the corneal tissue is partially elastic, the rim may be made of a relatively rigid material e.g. polymethylmethacrylate (PMMA) and still be inserted through the external opening 42 that is less than half of the diameter of the assembled corneal implant. The vertical dashed lines in the top of the figure and the circular dashed lines in the bottom figure represent an opening 76 left by a circular disk of anterior stromal tissue that has been excised (e.g. with a trephine). FIGS. 11C and 11D show that the optic 72 may fit into opening 76. FIGS. 11E and 11F show that the optic 72 has been attached to the two halves of the rim 70 and 74 to complete assembly of the corneal implant. The individual pieces of the corneal implant may be attached to each other by interlocking fittings (not shown), by glue, or any other appropriate mechanical or chemical method of fixation. In this embodiment of the invention the corneal implant is shown as a three piece prosthesis that replaces part of the cornea. However, it is to be understood that the invention includes any corneal implant that can be assembled as two or more pieces within a corneal pocket.

FIGS. 12A-12B are end views of the back of a deformation chamber 86 on a hollow member 80 which show how the presence of a protrusion 82 within the deformation chamber can help to maintain the orientation of a corneal implant 90 as it is pushed in an axial direction. Deformation chamber 86 includes three hinged sections 80*a*, 80*b*, and 80*c* which make up a hollow member which opens in order to receive corneal implant 90. At the lateral aspects of deformation area 80 are two protrusions 82, which help to hold the rim 94 of corneal implant 90 in place. FIG. 12B shows how sections 80*a*, 80*b*, and 80*c* can be closed by putting together the wings 84 (which together form an axial pusher or implant mover) to create hollow member 80 and deformation chamber 86. Corneal implant 90 is now securely fixated within the hollow deformation chamber 86 by the protrusions 82 and can be manipulated. The corneal implant 90 can then be moved axially along hollow member 80 by an axial pusher or other implant mover (not shown) without inadvertent rotation of the corneal implant.

Please note at least some portion of the corneal implant could be colored in any of the embodiments of the invention to enhance the aesthetic appearance of the eye or to decrease the amount of light exposure to the eye (e.g. for treatment of aniridia).

Referring now to FIGS. 13A and 13B, a corneal implant insertion device 200 includes a deformation chamber 202 defined by two-circular hinged sections 204. The hinged sections 204 are attached to wings 206 which permit the hinged sections to be closed in order to capture the corneal implant C, after the implant has been introduced into the deformation chamber, as shown in FIG. 13B.

Protrusions 210 having interior arcuate surfaces 212 are attached to the hinged sections 204 so that the surfaces 212 form radially inwardly directed ramps, as illustrated in FIG. 14A. Thus, after the corneal implant C is introduced into the deformation chamber 202, as illustrated in FIG. 13B, closure of the chamber using the wings 206 will curl the corneal implant C into a C-shaped profile, as shown in FIG. 14A. This can be an advantage over the corneal insertion tool embodiment of FIGS. 12A and 12B where the edges of the implant are held in a generally open configuration by the outwardly facing surfaces of protrusions 82.

In a specific embodiment of the corneal implant insertion device of the present invention, the corneal implant C comprises a lamellar corneal stromal endothelial transplant graft of approximately 9 mm in diameter and 100 µm to 200 µm in thickness. The deformation chamber 220 has a diameter or width D of approximately 9 mm in order to receive the corneal implant C such that its edges are disposed beneath the arcuate surfaces 212 of the protrusions 210, as illustrated in FIG. 13B.

Referring now to FIGS. 15A through 15D, a pusher shaft 230 having a forward member 232 may be advanced into the deformation chamber 202 of the corneal implant insertion device 200. The forward element 232 will have a profile which is similar to the shape of the hollow passage so that it can pass over the protrusions 210 and will typically be compressible so that it can pass into a tapered region 240 of the insertion device, as shown in FIG. 15D. Thus, the forward member 232 will first be introduced into the constant-diameter portion of the deformation chamber 202, as shown in FIG. 15B, and used to advance the corneal implant C forwardly. The shaft 30 and forward member 232 will continue to be advanced so that the corneal implant C is pushed from the distal tip of the tapered region 240, as shown in FIG. 15C.

As the corneal implant C is advanced, its edges will be curved or everted inwardly, as illustrated in FIGS. 14A through 14C. In FIG. 14A, the corneal implant C is shown as it is in FIG. 15A. As it advances forwardly, as shown in FIG. 15B, the corneal implant C is reduced in diameter with the edges being pushed radially inwardly, as shown in FIG. 14B. Finally, as the corneal implant C is released from the proximal tip of the tapered region 240, it has a significantly reduced diameter, as shown in FIG. 14C. It is particularly desirable that the corneal implant C be reduced in size to as great an extent as possible but that the leading tips of the implant not touch the interior surface, just as shown in FIG. 14C. This reduces the damage or trauma to the delicate corneal endothelial cells during the implantation protocol.

In an embodiment illustrated in FIGS. 16A-F, a graft C, such as a DSEK or DMEK graft, is placed stromal side down onto the surface of implant mover 300. Implant mover 300 has a flexible platform 310 which provides a loading area and which consists of a thin flexible material, such as a plastic. FIG. 16A shows the DSEK or DMEK graft C on the platform 310 from a top view. FIG. 16 B shows the DSEK or DMEK graft C on the platform 310 in side profile. FIG. 16E shows the DSEK or DMEK graft on the platform 310 from a front view at the start of the loading process. FIG. 16E is shown at the same time point of the loading process as FIGS. 16A and 16B. FIG. 16 C is a top view which shows that when platform 310 is pulled into a hollow member 320 by implant mover member 300 that the flexible platform 310 will become constrained in size and shape. Because the DSEK or DMEK graft C is flexible it will also become constrained in size and shape inside the flexible platform 310. FIG. 16 D shows a side view at the same time point as 16C. FIG. 16F shows how DSEK or DMEK graft C is restrained inside flexible platform 310 into a small diameter configuration. In FIGS. 16A-D and 16 F an internal arcuate protrusion 330 will force the flexible platform 310 and DSEK graft C to curl in a way that engages only the stromal surface, thereby protecting the delicate corneal endothelium located on the inside of the DSEK or DMEK Graft C. When DSEK or DMEK graft C is to be inserted into the anterior chamber, hollow member 320 is advanced into the corneal or scleral incision. Implant mover 300 is then advanced, allowing flexible platform 310 and DSEK Graft C so that DSEK Graft C can unfurl and be released into the anterior chamber. FIGS. 16A-D show an optional bevel to the end of hollow member 320 which advantageously allows for easier insertion into the ocular incision. The optional bevel has an angle between 1° and 89°, preferably between 25° and 65°.

FIG. 17A shows a top view of a corneal scaffold implant 400 which is designed for correcting myopia. The scaffold implant 400 is formed from discrete elements 402 which provide a peripheral shape which is a truncate dome. An interior volume of the dome is empty and free from structure. FIG. 17B is an oblique view which shows the shape of the cornea C prior to insertion of the corneal scaffold implant 400 for myopia into a corneal pocket through incision I. FIG. 17C shows how the insertion of corneal scaffold implant for myopia 400 flattens the cornea in the direction of the arrow 404 and thereby reduces myopia.

FIG. 18A shows a top view of a corneal scaffold implant 410 which is designed for the purpose of correcting hyperopia. The implant 410 comprises elements 412 which form a higher truncated dome than implant 400. FIG. 18B shows how the insertion of this corneal scaffold implant for hyperopia 410 steepens the cornea in the direction of the arrow and thereby reduces hyperopia.

FIG. 19A shows a top view of a corneal scaffold implant 420 which is designed for the purpose of correcting hyperopic astigmatism. The implant 420 comprises two lateral wings 422 joined by a central ring 424. FIG. 19B shows how the insertion of this corneal scaffold implant for hyperopic astigmatism 420 steepens the central cornea in the direction of the arrow and thereby reduces hyperopia and also flattens the steep axis of the cornea thereby reducing astigmatism.

FIG. 20A shows a top view of a corneal scaffold implant 430 which also contains a lens L shown in hatched lines. FIG. 20B shows how the insertion of this corneal scaffold implant with a lens 430 corrects refractive error by both changing the shape of the cornea (flattening in this case) and by introducing an additional lens to the optical system.

The scaffold may be formed from the same polymers as described previously by common techniques, such as molding. Many other shapes and structures for the corneal scaffold implant can be devised for the treatment of myopia, hyperopia, astigmatism, higher order aberrations and ectactic corneal diseases. Our invention includes all of the possible three dimensional shapes and structures where it is not possible for a single plane to pass through all of the elements of the structure.

Figure 21A:
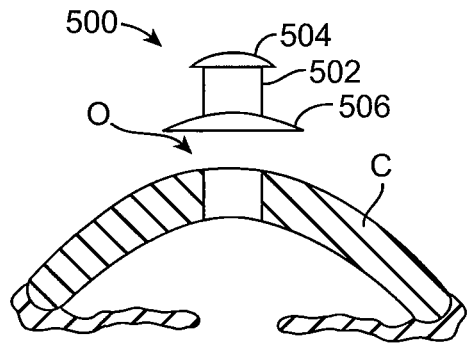
FIGS. 21A-C illustrate an implantation protocol useful for implanting the corneal implant illustrated in FIG. 8F.
Figure 21B:
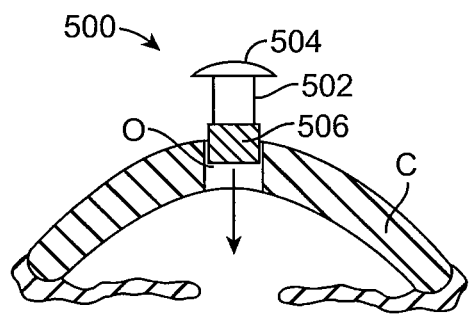
Figure 21C:
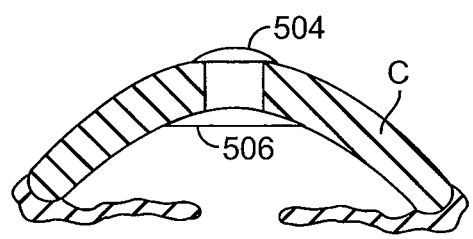

The corneal implant 500 described previously with reference to FIG. 8F can be reversibly deformed and inserted into a full-thickness opening O in a cornea C, as illustrated in FIGS. 21A-21C. The opening O will typically be smaller than the corneal implant 500 and, in order to insert the implant into the opening, at least the posterior rim will be constrained against the sidewall of the center optic 502, as shown in FIG. 21B. Such constraint may be achieved with the various insert apparatus, including the tapered tubes as described hereinbefore. Alternatively, the deformation could be achieved using conventional forceps or other surgical tools. The implant 502 is inserted fully so that the anterior rim 504 engages the upper surface of the cornea C in the region surrounding the opening O with the posterior rim 506 returning to its unconstrained state and engaging the anterior surface of the cornea, as illustrated in FIG. 21C. Thus, the rims 504 and 506 capture the anterior and posterior surfaces of the cornea to create a watertight seal. Optionally, sutures could be placed through the edges or peripheries of the rims 504 and 506, further optionally through holes (not shown), to secure the implant. Alternatively, the implant 500 could be introduced through a separate incision into the cornea with the anterior plate being constrained as the implant is pushed upwardly or in the anterior direction, with the anterior rim 504 emerging from the top surface and resuming an unconstrained geometry to capture the cornea.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An article of manufacture, comprising:
   (a) a corneal prosthesis for replacing corneal tissue;
   (b) said corneal prosthesis being reversibly deformable, with said corneal prosthesis comprising a relaxed state and a deformed state;
   (c) wherein said corneal prosthesis is capable of returning to said relaxed state from said deformed state;
   (d) wherein said corneal prosthesis in said deformed state is capable of being implanted into a cornea through an opening that is less than the width of said corneal prosthesis in said relaxed state;
   (e) said corneal prosthesis comprising a center optic comprising an anterior surface, a posterior surface, and a peripheral wall; and
   (f) wherein said corneal prosthesis comprises at least one rim circumscribing at least a portion of said peripheral wall, said at least one rim having a thickness less than the thickness of said center optic.

2. An article as in claim 1, wherein said corneal prosthesis reverts to said relaxed state after introduction into the cornea such that said at least one rim expands and engages corneal tissue to anchor said corneal prosthesis in place in the cornea.

3. An article as in claim 2, wherein said center optic and said at least one rim are constructed of a single material, said material being reversibly deformable.

4. An article as in claim 3, wherein said corneal prosthesis comprises a monolithic structure free from discontinuities, joints, adhesions, and connections.

5. An article as in claim 3, wherein said material has a tensile strength in the range from 0.1 MPa to 4 MPa and a modulus in the range from 0.1 MPa to 5 Mpa.

6. An article as in claim 3, wherein said center optic extends anteriorly from said at least one rim.

7. An article as in claim 1, wherein said center optic comprises an anterior edge and a posterior edge, and wherein said at least one rim circumscribes said peripheral wall of said center optic around said posterior edge of said center optic.

8. An article as in claim 1, wherein said center optic comprises an anterior edge and a posterior edge, and wherein said at least one rim circumscribes said peripheral wall of said center optic between said anterior edge and said posterior edge of said center optic.

9. An article as in claim 1, wherein said deformed state is characterized by a rolling of said corneal prosthesis toward the center of said corneal prosthesis.

10. An article as in claim 9, wherein no portion of said corneal prosthesis contacts any other portion of said corneal prosthesis when said corneal prosthesis is in said deformed state.

11. An article as in claim 10, wherein said corneal prosthesis unfurls after implantation into the cornea.

12. An article as in claim 1, wherein said corneal prosthesis comprises a material selected from the group consisting of acrylic, silicone, and collagen copolymer.

13. An article as in claim 1, wherein said corneal prosthesis returns to said relaxed state after implantation into the cornea.

14. An article as in claim 1, wherein said center optic is shaped to replace corneal tissue removed from the cornea, and has a thickness sized to replace the corneal tissue removed from the cornea.

15. An article as in claim 1, wherein when said corneal prosthesis is implanted into a cornea, said at least one rim anchors said corneal prosthesis in the cornea.

16. An article as in claim 15, wherein said at least one rim anchors said corneal prosthesis in the cornea without sutures.

* * * * *